(12) United States Patent
Fujii

(10) Patent No.: US 10,470,867 B2
(45) Date of Patent: Nov. 12, 2019

(54) MEDICAL DEVICE

(71) Applicant: TERUMO KABUSHIKI KAISHA, Shibuya-ku, Tokyo (JP)

(72) Inventor: Tatsunori Fujii, Ebina (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 349 days.

(21) Appl. No.: 14/869,562

(22) Filed: Sep. 29, 2015

(65) Prior Publication Data
US 2016/0157878 A1    Jun. 9, 2016

(30) Foreign Application Priority Data

Dec. 4, 2014 (JP) ................................. 2014-246087

(51) Int. Cl.
*A61B 17/22* (2006.01)
*A61D 1/02* (2006.01)
(Continued)

(52) U.S. Cl.
CPC ........ *A61F 2/062* (2013.01); *A61B 17/00008* (2013.01); *A61B 17/3205* (2013.01);
(Continued)

(58) Field of Classification Search
CPC . A61F 2/06; A61B 17/3205; A61B 17/00008; A61B 90/361; A61B 2017/00778; A61B 2017/320064
See application file for complete search history.

(56) References Cited

U.S. PATENT DOCUMENTS 3,472,231 A * 10/1969 Niebel ................ A61B 17/1114
606/142
5,817,013 A * 10/1998 Ginn .................... A61B 1/0014
600/114
(Continued)

FOREIGN PATENT DOCUMENTS

JP    2003199765 A    7/2003
JP    2008253785 A    10/2008

OTHER PUBLICATIONS

Souza "The future of saphenous vein graft for coronary bypass surgery" Rev Bras Cir Cardiovasc vol. 23 No. 3 Jul./Sep. 2008.*
(Continued)

*Primary Examiner* — Amy R Weisberg
(74) *Attorney, Agent, or Firm* — Buchanan Ingersoll & Rooney PC

(57) ABSTRACT

A blood vessel dissecting device includes: a dissecting device which, when inserted into a living body along a blood vessel, dissects tissue in a direction of alignment of the dissecting device with the blood vessel; and a cutting device which, when inserted into the living body along the blood vessel, cuts tissue surrounding the blood vessel in a direction of alignment of the cutting device with the blood vessel. A blood vessel dissecting method includes: inserting a dissecting device into a living body along a blood vessel so as to dissect tissue in a direction of alignment of the dissecting device with the blood vessel; and inserting a cutting device into the living body along the blood vessel while guiding the cutting device with the dissecting device so as to cut tissue surrounding the blood vessel in a direction of alignment of the cutting device with the blood vessel.

20 Claims, 19 Drawing Sheets

(51) Int. Cl.

| | | |
|---|---|---|
| *A61F 2/06* | (2013.01) | |
| *A61B 17/3205* | (2006.01) | |
| *A61B 17/00* | (2006.01) | |
| *A61B 90/00* | (2016.01) | |
| *A61B 18/14* | (2006.01) | |
| *A61B 17/32* | (2006.01) | |
| *A61B 18/00* | (2006.01) | |
| *A61B 90/30* | (2016.01) | |

(52) U.S. Cl.
 CPC ........ *A61B 18/1482* (2013.01); *A61B 90/361* (2016.02); *A61F 2/06* (2013.01); *A61B 90/30* (2016.02); *A61B 2017/00778* (2013.01); *A61B 2017/00969* (2013.01); *A61B 2017/320044* (2013.01); *A61B 2017/320064* (2013.01); *A61B 2018/00428* (2013.01); *A61B 2018/1412* (2013.01)

(56) References Cited

U.S. PATENT DOCUMENTS

| | | | | |
|---|---|---|---|---|
| 5,993,472 | A * | 11/1999 | Hermann | A61B 17/00008 606/190 |
| 6,030,406 | A * | 2/2000 | Davis | A61B 17/00008 604/104 |
| 6,036,713 | A * | 3/2000 | Kieturakis | A61B 17/00008 606/159 |
| 6,165,175 | A * | 12/2000 | Wampler | A61B 17/00008 606/41 |
| 6,193,653 | B1 * | 2/2001 | Evans | A61B 17/00008 600/210 |
| 6,551,314 | B1 * | 4/2003 | Hill | A61B 17/00008 606/45 |
| 7,981,127 | B2 | 7/2011 | Kasahara et al. | |
| 2003/0130654 | A1 * | 7/2003 | Kasahara | A61B 17/3421 606/45 |
| 2003/0130674 | A1 * | 7/2003 | Kasahara | A61B 17/00008 606/159 |
| 2003/0130675 | A1 * | 7/2003 | Kasahara | A61B 17/00008 606/159 |
| 2005/0096645 | A1 * | 5/2005 | Wellman | A61B 17/320016 606/41 |
| 2005/0159764 | A1 * | 7/2005 | Kasahara | A61B 17/00008 606/159 |
| 2005/0192613 | A1 * | 9/2005 | Lindsay | A61B 17/00008 606/190 |
| 2006/0235450 | A1 * | 10/2006 | Kasahara | A61B 17/3421 606/159 |
| 2006/0276815 | A1 | 12/2006 | Lotti et al. | |
| 2008/0249556 | A1 | 10/2008 | Yamatani | |
| 2008/0255407 | A1 * | 10/2008 | Blakeney | A61B 17/00008 600/36 |
| 2010/0292533 | A1 * | 11/2010 | Kasahara | A61B 1/012 600/104 |
| 2013/0274548 | A1 * | 10/2013 | Fels | A61B 17/00008 600/104 |
| 2014/0296847 | A1 * | 10/2014 | Chin | A61B 17/3205 606/41 |
| 2014/0378957 | A1 * | 12/2014 | Orphanos | A61B 17/3205 606/14 |
| 2016/0007838 | A1 * | 1/2016 | Ariura | A61B 1/00087 600/37 |
| 2016/0045216 | A1 * | 2/2016 | Langford | A61B 17/320016 606/29 |
| 2016/0058442 | A1 * | 3/2016 | Russo | A61B 17/0644 606/151 |
| 2016/0157878 | A1 * | 6/2016 | Fujii | A61B 17/00008 606/167 |
| 2016/0242839 | A1 * | 8/2016 | Jinno | A61B 18/1445 |
| 2016/0367279 | A1 * | 12/2016 | Orphanos | A61B 17/320016 |
| 2017/0100106 | A1 * | 4/2017 | Jinno | A61B 17/00008 |
| 2017/0100107 | A1 * | 4/2017 | Takashi | A61B 17/00008 |
| 2017/0100108 | A1 * | 4/2017 | Fujii | A61B 17/00008 |
| 2017/0100109 | A1 * | 4/2017 | Takashi | A61B 17/00008 |
| 2017/0100152 | A1 * | 4/2017 | Fujii | A61B 17/32053 |
| 2017/0128056 | A1 * | 5/2017 | Takashi | A61B 17/00008 |
| 2017/0189051 | A1 * | 7/2017 | Fujii | A61B 17/32053 |
| 2017/0189052 | A1 * | 7/2017 | Fuji | A61B 17/32053 |
| 2017/0189053 | A1 * | 7/2017 | Otsubo | A61B 17/32053 |
| 2017/0189054 | A1 * | 7/2017 | Fujii | A61B 17/32053 |
| 2017/0189055 | A1 * | 7/2017 | Suehara | A61B 17/32053 |
| 2017/0245845 | A1 * | 8/2017 | Fujii | A61B 17/00008 |
| 2017/0245910 | A1 * | 8/2017 | Jinno | A61B 18/082 |
| 2017/0245922 | A1 * | 8/2017 | Fujii | A61B 18/1445 |

OTHER PUBLICATIONS

Souza et al., "The no-touch technique of harvesting the saphenous vein for coronary artery bypass grafting surgery", Multimedia Manual of Cardiothoracic, European Association for Cardio-thoracic Surgery, 2009 (month unknown), pp. 1-6.

Notification of Transmittal of Translation of the International Preliminary Report on Patentability (Forms PCT/IB/338 and PCT/IB/373) and the Written Opinion of the International Searching Authority (Form PCT/ISA/237) dated Jun. 6, 2017, by the International Bureau of WIPO in corresponding International Application No. PCT/JP2015/071656. (7 pgs).

* cited by examiner

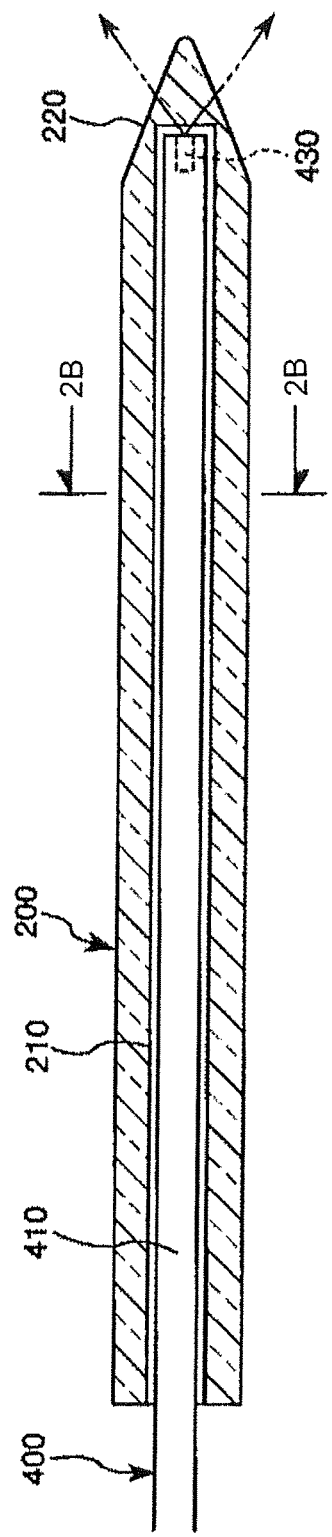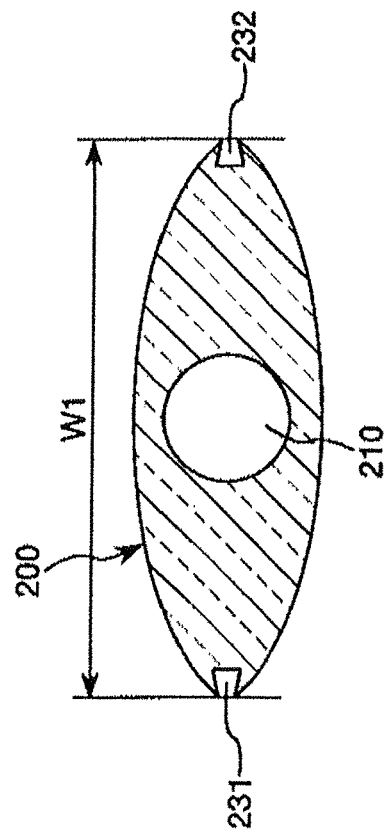
FIG. 2A
FIG. 2B

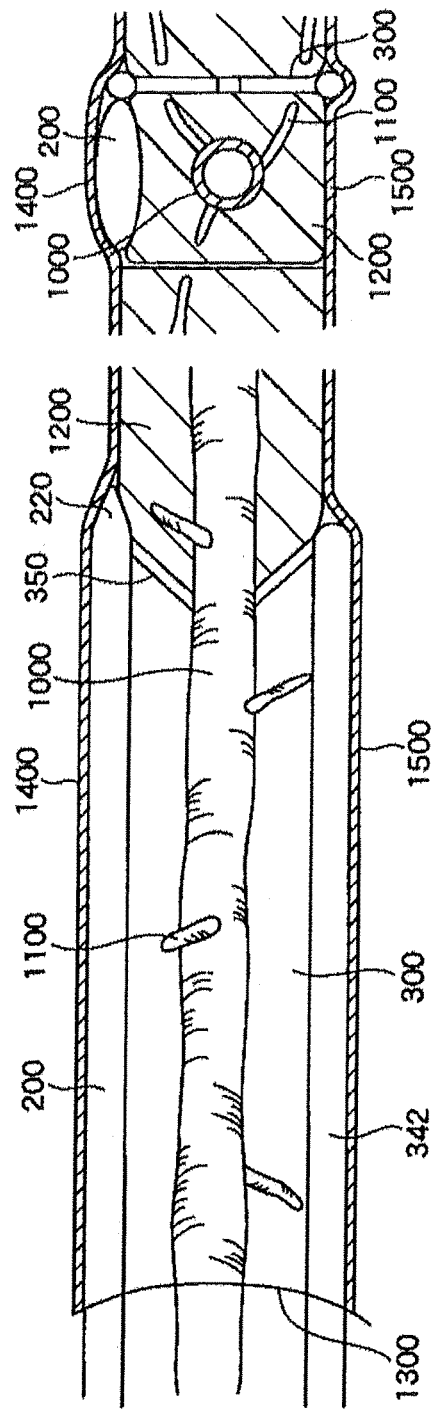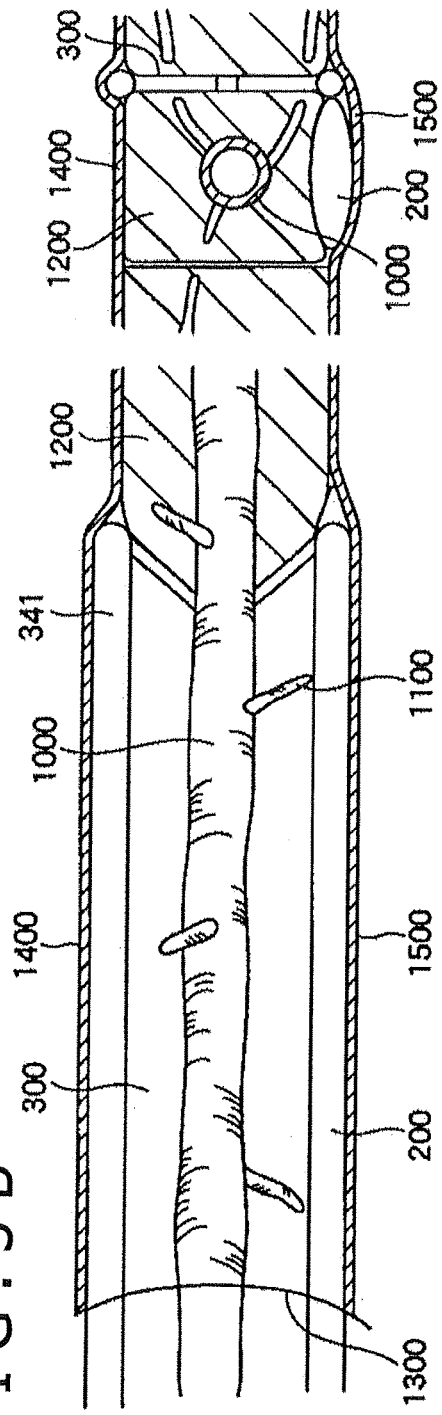

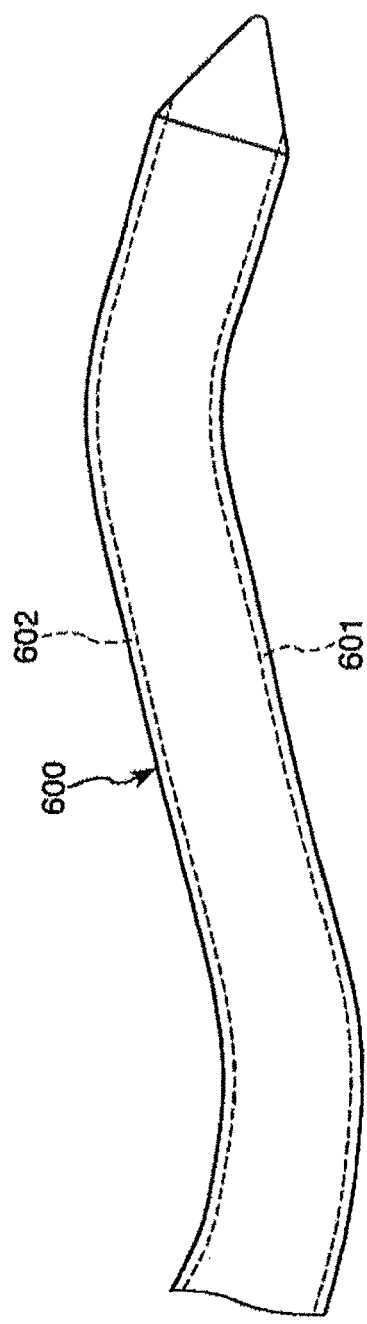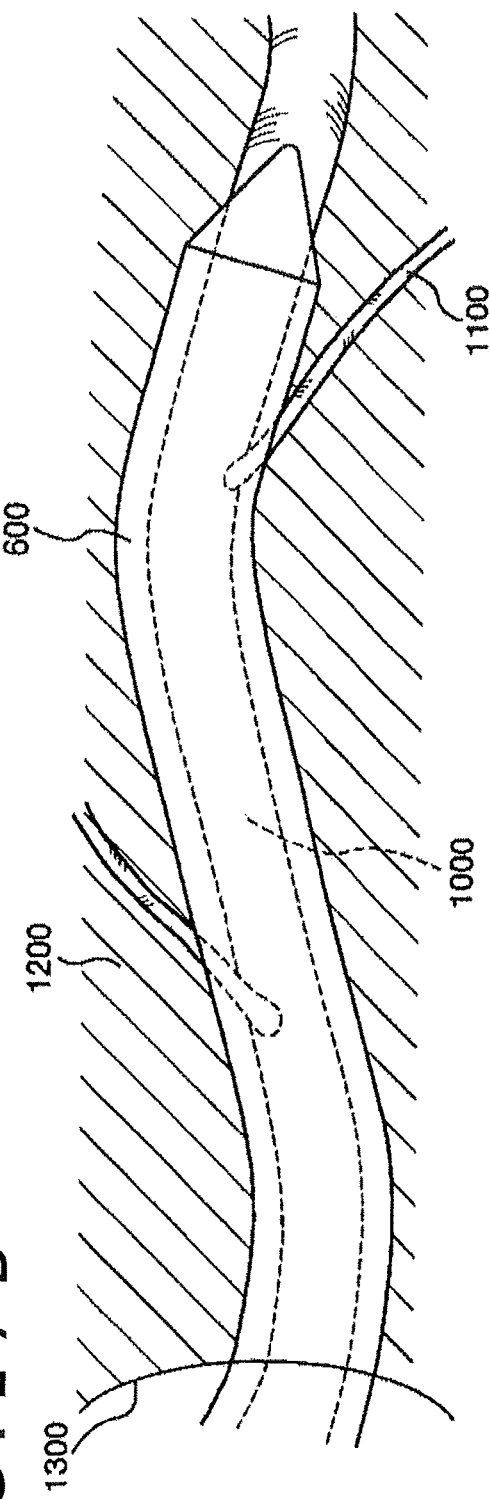
FIG. 17A
FIG. 17B

MEDICAL DEVICE

CROSS-REFERENCES TO RELATED APPLICATIONS

This application is based on and claims priority to Japanese Application No. 2014-246087 filed on Dec. 4, 2014, the entire content of which is incorporated herein by reference.

TECHNICAL FIELD

The present disclosure relates to a blood vessel dissecting device and a blood vessel dissecting method.

BACKGROUND DISCUSSION

It is known to use an artery graft represented by internal thoracic artery, gastroepiploic artery and radial artery or a vein graft represented by great saphenous vein as a bypass vessel in performing vascular bypass grafting at the heart (coronary artery bypass grafting: CABG). Besides, at present, it has been reported that artery grafts (particularly, internal thoracic artery) offer higher long-term patency rates than vein grafts. Thus, vein grafts are commonly said to be poor in long-term patency rate. In recent years, however, it has been reported that the long-term patency rate concerning a vein graft is enhanced when the vein graft is harvested in the state of being covered with the surrounding tissue (for example, fat, connective tissue, tissue between a skin layer and a muscle layer, tissue between a skin layer and an interosseous membrane, branch vessels, etc.) and is used as a bypass vessel while remaining covered with the tissue. U.S. Application Publication No. 2006/0276815 describes an example of a device by which a vein graft can be harvested in the state of being covered with the surrounding tissue.

In using the device disclosed in U.S. Application Publication No. 2006/0276815, a guide wire (support member 50) is inserted into a blood vessel to be harvested as a bypass vessel, and a tubular member (portion 40) is pushed forward while guiding it with the guide wire, whereby the blood vessel can be harvested in the state of being covered with the surrounding tissue. The device disclosed in US 2006/0276815, however, has drawbacks in that the guide wire may damage the internal wall of the blood vessel being harvested and that the workability in blood vessel harvesting (blood vessel dissection) is poor.

SUMMARY

Thus, there is a need for a blood vessel dissecting device and a blood vessel dissecting method by which a blood vessel can be dissected with good workability.

Disclosed here is a blood vessel dissecting device including: a dissecting device which is configured to be inserted into a living body along a blood vessel to dissect tissue in a direction along the longitudinal extent of the blood vessel; and a cutting device configured to be inserted into the living body along the longitudinal extent of the blood vessel to cut tissue surrounding the blood vessel in the direction of longitudinal extent of the blood vessel.

In the blood vessel dissecting device as above, preferably, the dissecting device has a flat-shaped cross-section, and is inserted into the living body so as to be aligned with the blood vessel in a thickness direction of the dissecting device.

In the blood vessel dissecting device, a width of the dissecting device may be greater than an outside diameter of the blood vessel.

In using the blood vessel dissecting device, preferably, the dissecting device is inserted between adjacent tissues having different properties.

In the blood vessel dissecting device, the cutting device may include: a cutting section adapted to cut the tissue surrounding the blood vessel; and a treating section adapted to cut and stanch a branch vessel branched from the blood vessel.

In the blood vessel dissecting device, preferably, the dissecting device and the cutting device can be connected to each other.

Another aspect of the disclosure here involves a blood vessel dissecting method including: inserting a dissecting device into a living body along a blood vessel to dissect tissue in a direction along a longitudinal extent of the blood vessel; and inserting a cutting device into the living body along the blood vessel while using the dissecting device to guide the cutting device to cut tissue surrounding the blood vessel in the direction of longitudinal extent of the cutting device.

In the blood vessel dissecting method as above, preferably, the dissecting device is inserted between adjacent tissues having different properties.

According to the described aspects, the blood vessel dissecting device includes the dissecting device for dissecting tissue, and the cutting device for cutting fat. This configuration helps ensure relatively easy dissection of a blood vessel from a living body. Specifically, when treating a part which is easy to dissect, the dissecting device is used so as to reduce such damage as bleeding. On the other hand, when treating fat which is comparatively difficult to dissect, the cutting device is used to cut the fat. By this method, the blood vessel to be harvested can be dissected smoothly and with minimal invasiveness. Especially, by inserting the dissecting device between tissues which have different properties, tissue dissection can be achieved more smoothly.

BRIEF DESCRIPTION OF THE DRAWINGS

FIGS. 2A and 2B illustrate a dissecting device forming a part of the blood vessel dissecting device shown in FIG. 1, wherein FIG. 2A is a longitudinal cross-sectional view and FIG. 2B is a transverse cross-sectional view taken along the section line 2B-2B of FIG. 2A.

FIGS. 3A and 3B illustrate a cutting device forming a part of the blood vessel dissecting device shown in FIG. 1, wherein FIG. 3A is a plan view and FIG. 3B is a cross-sectional view taken along the section line 3B-3B of FIG. 3A.

FIGS. 5A and 5B show views explaining the blood vessel dissecting method carried out using the blood vessel dissecting device shown in FIG. 1.

FIGS. 12A to 12C illustrate a dissecting device forming a part of a blood vessel dissecting device according to a sixth embodiment of the present disclosure, wherein FIG. 12A is a top plan view, FIG. 12B is a side view, and FIG. 12C is a top plan view showing the dissecting device in the state of being used.

FIGS. 13A and 13B illustrate a dissecting device forming a part of a blood vessel dissecting device according to a seventh embodiment of the present disclosure, wherein FIG. 13A is a top plan view and FIG. 13B is a top plan view showing the dissecting device in the state of being used.

FIGS. 17A and 17B are plan views of a dissecting device forming a part of a blood vessel dissecting device according to an eleventh embodiment of the present disclosure.

DETAILED DESCRIPTION

Examples of a blood vessel dissecting device and a blood vessel dissecting method disclosed here will be described in detail below, referring to the attached drawings.

First Embodiment

Figure 1:
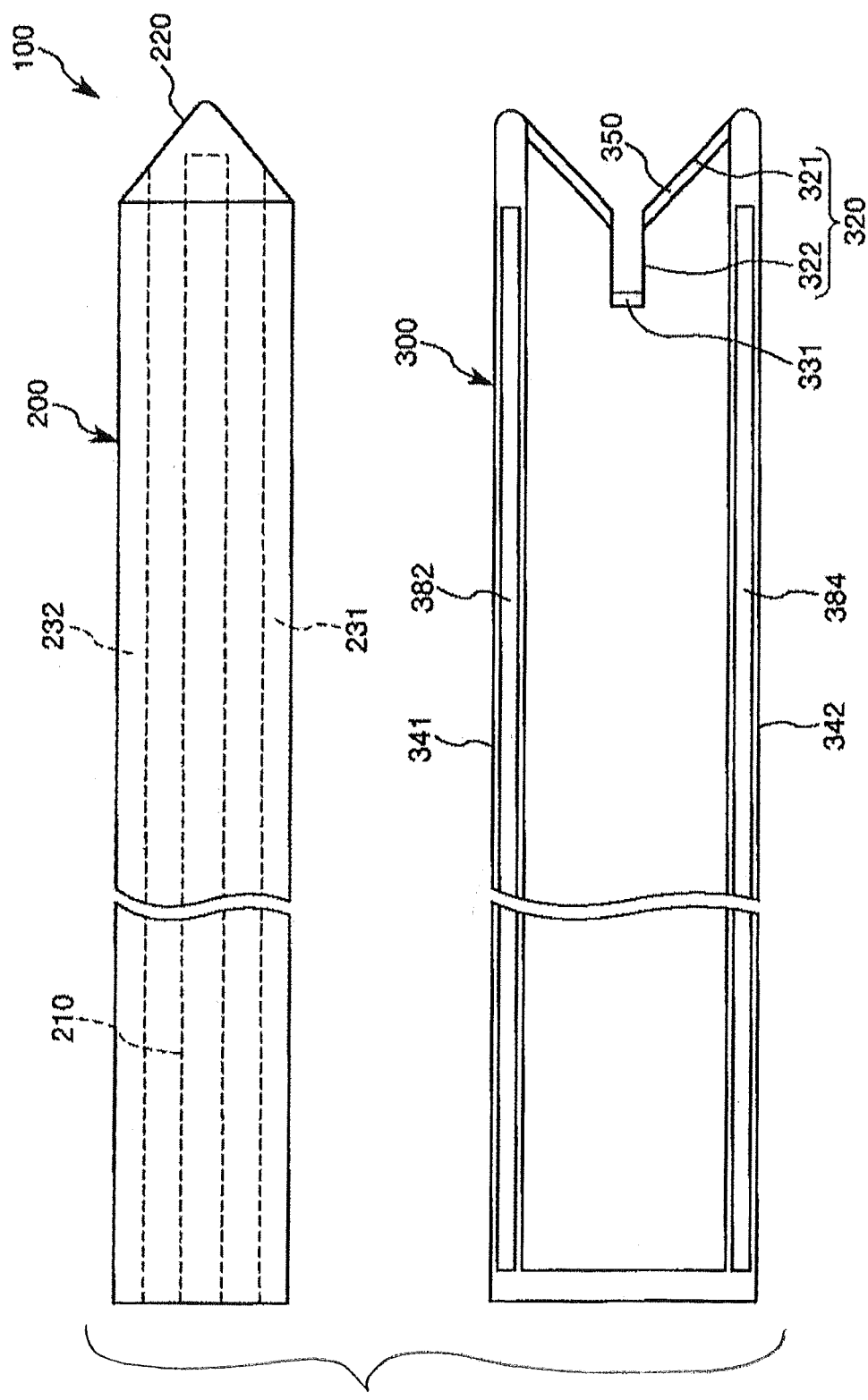
FIG. 1 is a plan view of a blood vessel dissecting device according to a first embodiment of the present disclosure.

FIGS. 1-5b illustrate a blood vessel dissecting device and blood vessel dissecting method carried out using the blood vessel dissecting device according to a first embodiment representing one example of the disclosure here. In the following description, for convenience of explanation, the right side in FIG. 1 will be referred to as "distal" side or end, and the left side in the figure as "proximal" side or end.
Blood Vessel Dissecting Device A blood vessel dissecting device 100 shown in FIG. 1 is a device used to harvest a blood vessel for use as a bypass vessel in carrying out blood vessel bypass grafting (particularly, coronary artery bypass grafting: CABG). By use of the blood vessel dissecting device 100, a blood vessel can be harvested in the state of being covered with the surrounding tissue (fat, connective tissue, etc.). Note that the blood vessel to be harvested using the blood vessel dissecting device 100 is not particularly limited insofar as it is a blood vessel that can be used as a bypass vessel. Examples of the applicable blood vessel include internal thoracic artery, gastroepiploic artery, radial artery, and great saphenous vein.

It is preferable, however, that the blood vessel to be harvested is the great saphenous vein. As aforementioned, the use of the blood vessel dissecting device 100 facilitates harvesting of a blood vessel in the state in which the blood vessel is covered with the surrounding tissue. When the great saphenous vein is harvested by using the blood vessel dissecting device 100 and is used as a bypass vessel, therefore, it is considered that an enhanced long-term patency rate is obtained after the bypass grafting operation. In view of this, in the following, an example of harvesting a great saphenous vein by use of the blood vessel dissecting device 100 will be described on a representative basis.

As shown in FIG. 1, the blood vessel dissecting device 100 includes a dissecting device 200 and a cutting device 300. Both the dissecting device 200 and the cutting device 300 are devices which are inserted into a living body along the great saphenous vein. The dissecting device 200 and the cutting device 300 will now be described in detail below.
Dissecting Device The dissecting device 200 has an elongated bar-like shape (bar-shaped) extending substantially straight, and is provided at its distal end with a dissecting section 220 for dissecting tissue. In addition, as shown in FIG. 2B, the dissecting device 200 has a flat shape (vertically flattened shape as seen in transverse cross-section) in section. The cross-sectional shape of the dissecting device 200 is not specifically restricted; for example, the cross-sectional shape may be a crushed-circle-like shape (flattened circular shape), such as an oblong and an ellipse, a rectangle rounded at corners, or the like.

The width (the length in the major axis direction of the cross-sectional shape) W1 of the dissecting device 200 is greater than the outside diameter of the blood vessel to be harvested (in this embodiment, the great saphenous vein). To be more specific, the width W1 is preferably about 4 mm to 2 cm greater than the outside diameter of the blood vessel to be harvested. This helps ensure that the possibility of contact between the cutting device 300 and the great saphenous vein can be effectively lowered at the time of inserting the cutting device 300 into the living body along the dissecting device 200, as will be explained in the "blood vessel harvesting method" described later.

In addition, the dissecting device 200 is provided, at both ends of the major axis of the cross-sectional shape thereof, with rails 231 and 232 in the form of linear stretches of recess (or trenches/grooves) which extend in the axial direction of the dissecting device 200. Each of the rails 231 and 232 is used for connection of the dissecting device 200 with the cutting device 300, and functions as a guide section for guiding the cutting device 300. Note that the rails 231 and 232 are not limited to the linear stretches of recess (or trenches/grooves) but may be, for example, linear stretches of projection (or ridges or ribs), insofar as they each enable connection of the dissecting device 200 with the cutting device 300.

As shown in FIG. 2A, the dissecting device 200 is provided with an insertion hole 210 which opens at the proximal end and extends to a distal portion (the dissecting section 220). In this illustrated embodiment, the insertion hole 210 is a blind hole, meaning the insertion hole 210 is closed at its distal end. Into the insertion hole 210 is inserted an imaging device 400. The imaging device 400 is not specifically restricted. For example, the imaging device 400 in this embodiment, as depicted in FIG. 2A, includes an elongated main body section 410, and an illuminating section (not shown) for emitting illumination light and an imaging section 430 for imaging the front side of the dissecting device 200. The illuminating section and the imaging section 430 are disposed at a distal portion of the main body section 410. The imaging section 430 includes, for example, an objective lens system disposed at the distal portion of the main body section 410 and an imaging element (e.g., solid state image sensor such as CMOS image sensor or CCD sensor) disposed opposite to the objective lens system.

The dissecting section 220 is tapered in a narrowing manner toward the distal end of the dissecting device 200. More specifically, the distal end portion of the dissecting section 220 possesses a tapered roughly conical shape so that the length in the minor axis direction and the length in the major axis direction of the cross-sectional shape of the dissecting section 220 are both gradually decreased in a direction toward the distal end. Such a dissecting section 220 is blunt in the thickness direction, and has such a degree of sharpness (bluntness) as to be able to dissect tissues having different properties (for example, fat and skin, fat and fascia, fat and blood vessel, fat and bone, etc.) from each other without cutting branch vessels branched from the great saphenous vein. This helps ensure that a dissecting function can be sufficiently exhibited and the branch vessels are restrained from being damaged or cut by the dissecting section 220. Accordingly, bleeding can be suppressed, and the intended technique can be performed safely and smoothly. Note that the shape of the dissecting section 220 is not particularly limited insofar as it enables dissection of tissues in the thickness direction (minor axis direction) of the tissues. For example, the dissecting section 220 may be in the shape of a duck bill such that the length in the minor axis direction of the cross-sectional shape of the dissecting section 220 is gradually decreased (tapered) toward the distal end and the cross-sectional shape at the distal end is a line segment along the major axis direction.

The dissecting section 220 is substantially colorless and transparent and is light-transmitting. This helps ensure that when the imaging device 400 is inserted into the insertion hole 210, the front side of the dissecting device 200 can be observed through the dissecting section 220 by the imaging device 400. In other words, the dissecting section 220 has the function as an observation section for observation of the inside of the living body (the great saphenous vein and its surroundings), in addition to the aforementioned function as the dissecting section. Note that the dissecting section 220 is not limited to the colorless transparent property but may be colored in red, blue, green or the like, insofar as it is light-transmitting.

Cutting Device

The cutting device 300, at the time of moving along a great saphenous vein 1000, cuts the fat (inclusive of connective tissue) surrounding the great saphenous vein 1000 and, in addition, cuts and stanches the branch vessels branched from the great saphenous vein 1000.

Figure 3A:
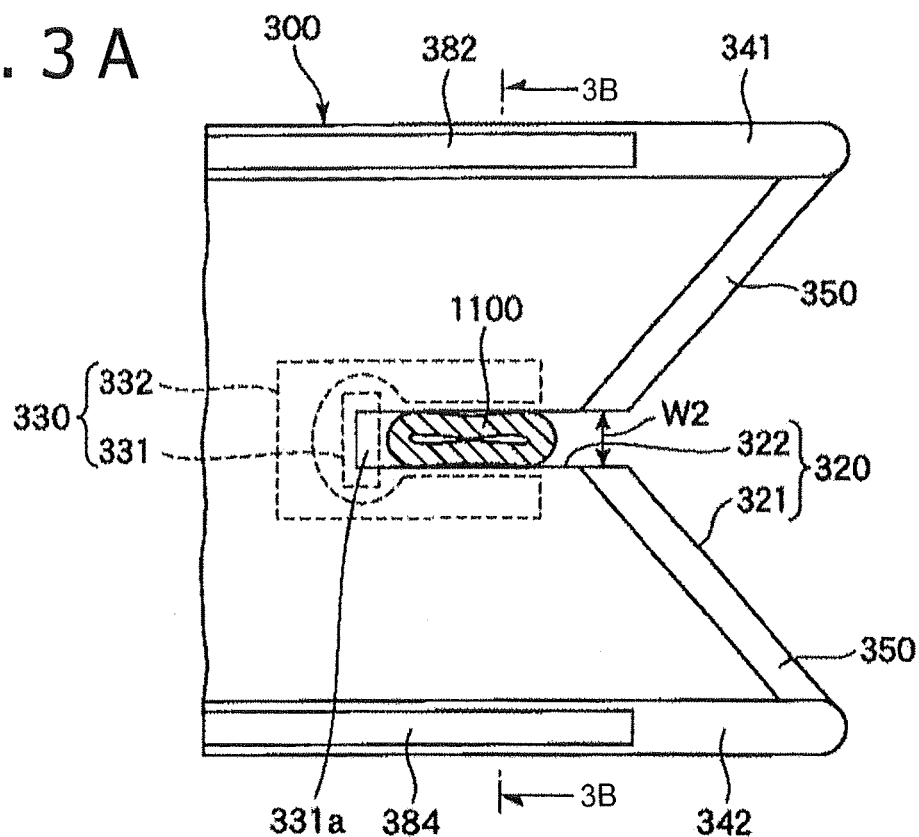

The cutting device 300 is elongated plate-like in shape (plate-shaped). As shown in FIGS. 1 and 3A, the cutting device 300 has a groove portion 320 opening in a distal portion of the cutting device. The groove portion 320 includes: a tapered blood vessel guide groove section (first groove section) 321 having a width gradually decreasing toward the proximal side; and a straight blood vessel treating groove section (second groove section) 322 which is located on the proximal side of the blood vessel guide groove section 321 and is substantially constant in width. The blood vessel guide groove section 321 is a groove section for guiding a branch vessel into the blood vessel treating groove section 322 at the time of pushing the cutting device 300 forward in a living body, and is tapered in shape for the guiding to be smoothly achieved. On the other hand, the blood vessel treating groove section 322 is a groove section for cutting and stanching the branch vessel guided to the blood vessel treating groove section 322 by the blood vessel guide groove section 321. Further, the blood vessel treating groove section 322 is provided with a treating section 330 for cutting and stanching a branch vessel.

As shown in FIG. 3A, the treating section 330 has a bipolar structure including a pair of electrodes 331 and 332 configured to generate an electric field inside the blood vessel treating groove section 322. The electrode 331 is disposed at a proximal end portion of the blood vessel treating groove section 322, while the electrode 332 is disposed on both sides with respect to the width direction of the blood vessel treating groove section 322. With a high-frequency AC voltage impressed between the electrodes 331 and 332, it is possible to heat and cut a branch vessel 1100 guided into the blood vessel treating groove section 322 and to stanch the blood vessel through thermal coagulation. A distal portion (a portion exposed to the blood vessel treating groove section 322) 331a of the electrode 331 is preferably so sharp as to be able to cut the branch vessel 1100. This helps ensure that if thermal coagulation (stanching) of the branch vessel 1100 can at least be achieved by the electric field generated between the electrodes 331 and 332, the branch vessel 1100 can be physically cut by the distal portion 331a of the electrode 331. Accordingly, the assuredness of the treatment by the treating section 330 is enhanced.

The width W2 of the blood vessel treating groove section 322 is not particularly limited but it is preferably narrower than the outside diameter of the branch vessel 1100. This helps ensure that the branch vessel 1100 can be pressed flat inside the blood vessel treating groove section 322 as shown in FIG. 3A, and, consequently, the treatment (cutting and stanching) at the treating section 330 can be performed more reliably.

The cutting device 300 is provided with a cutting edge section (cutting section) 350 for cutting the fat surrounding the great saphenous vein 1000. The cutting edge section 350 is disposed at a distal portion of the cutting device 300; in this embodiment, it is disposed along the blood vessel guide groove section 321. As will be explained also in the "blood vessel harvesting method" described later, the cutting edge section 350 has the function of cutting the fat surrounding the great saphenous vein 1000 at the time of pushing the cutting device 300 forward in the living body. Such a cutting edge section 350 preferably has such a sharpness as to be able to cut the fat without cutting the branch vessel 1100. This helps ensure that cutting of the branch vessel 1100 by the cutting edge section 350 is inhibited, so that bleeding is restrained, and the intended technique can be performed safely and smoothly.

Figure 3B:
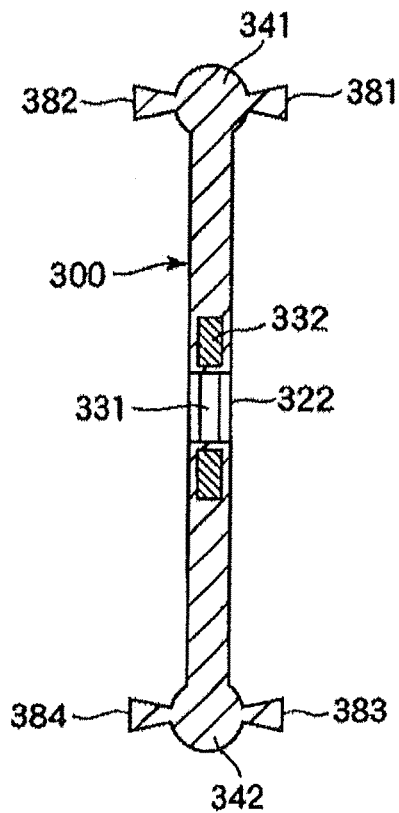

As shown in FIG. 3B, the cutting device 300 has a pair of protection sections 341 and 342 provided on both sides with respect to the cutting device's width direction (the direction orthogonal to its moving direction). The protection sections 341 and 342 each extend along the axial direction of the cutting device 300, and their peripheral surfaces (side surfaces and distal surfaces) are rounded. As will be explained also in the "blood vessel harvesting method" described later, the protection section 341 moves along and between fat and skin while dissecting them from each other, at the time of pushing the cutting device 300 toward the distal side in a living body. Since the fat and the skin having different properties, they are rather easy to dissect from each other, even though the distal end portion of the protection section 341 is rounded, and the dissecting function of dissecting the fat and the skin from each other can be exhibited sufficiently. In addition, the rounding helps ensure that a branch vessel can be restrained from being damaged or cut by the protection section 341, and, further, damage to (cauterization of) the skin due to sliding against (friction with) the protection section 341 can be restrained. Similarly, the protection section 342 moves along and between the fat and the fascia while dissecting them from each other at the time of pushing the cutting device 300 toward the distal side in the living body. Since the fat and the fascia having different properties, they are easy to dissect from each other, even though a distal end portion of the protection section 342 is rounded, and the dissecting function of dissecting the fat and the fascia from each other can be exhibited sufficiently. Besides, the rounding helps ensure that the branch vessel can be restrained from being damaged or cut by the protection section 342, and, further, damage to (cauterization of) the fascia due to sliding against (friction with) the protection section 342 can be restrained.

As shown in FIGS. 3A and 3B, the cutting device 300 has connection sections 381, 382, 383 and 384 configured to connect with the rails 231 and 232 of the dissecting device 200. The connection sections 381 and 382 are provided at the protection section 341, and disposed on mutually opposite surface sides. Similarly, the connection sections 383 and 384 are provided at the protection section 342, and disposed on mutually opposite surface sides. These connection sections 381 to 384 are composed of stretches (lengths) of projection (or ridges or ribs) which extend in the axial direction of the cutting device 300 and correspond to the stretches of recess (trenches) of the rails 231 and 232. Since such connection sections 381 to 384 are provided, unintended detachment of the dissecting device 200 and the cutting device 300 from each other is prevented, so that the intended technique can be carried out more smoothly and accurately. Thus, in this example of the blood vessel dissecting device, both the cutting device 300 and the dissecting device 200 include connection structure configured to connect the cutting device 300 and the dissecting device 200 to each other.

Blood Vessel Harvesting Method

A method of harvesting a blood vessel by use of the blood vessel dissecting device 100 includes: a first step (blood vessel dissecting method) of dissecting the great saphenous vein 1000 in the state of being covered with surrounding fat 1200 by use of the blood vessel dissecting device 100; a second step of ligating the great saphenous vein 1000 and then cutting the great saphenous vein 1000; and a third step of extracting the great saphenous vein 1000 in the state of being covered with the surrounding fat 1200 from the living body.

First Step

Figure 4A:
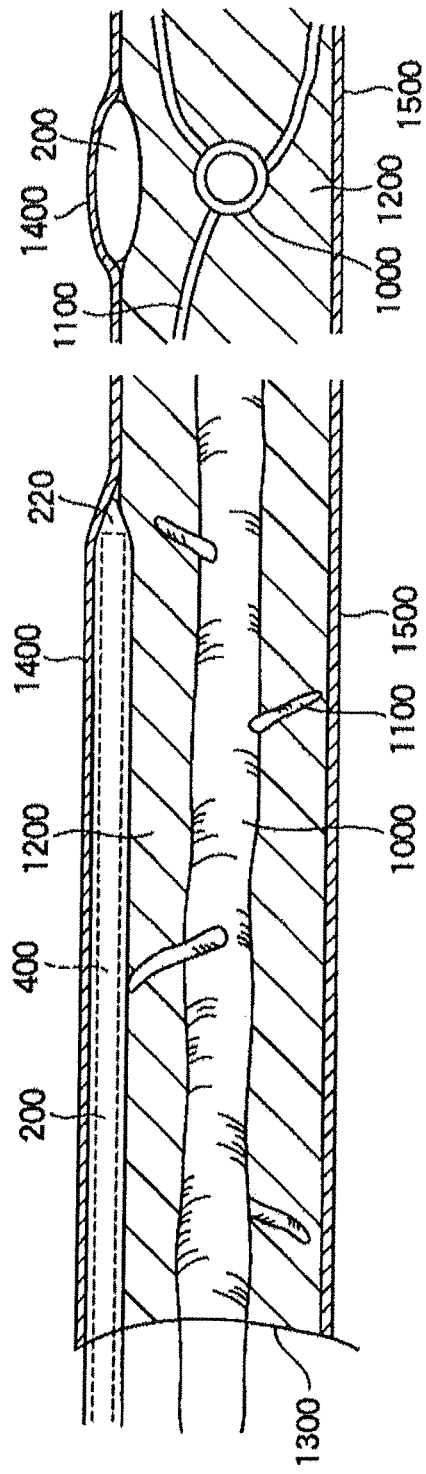
FIGS. 4A and 4B show views explaining a blood vessel dissecting method carried out using the blood vessel dissecting device shown in FIG. 1.

First, the position of the great saphenous vein 1000 to be harvested is confirmed, and skin is incised on the basis of the position of the great saphenous vein. Next, the dissecting device 200 with the imaging device 400 inserted in the dissecting device 200 is prepared, and, while observing the inside of the living body by the imaging device 400, the dissecting device 200 is inserted from the incision 1300 into the living body along the great saphenous vein 1000 while keeping the dissecting device 200 spaced from the great saphenous vein 1000. Then, as shown in FIG. 4A, the dissecting device 200 is disposed on the upper side (the skin 1400 side) of the great saphenous vein 1000. In this case, the dissecting device 200 is so disposed that the thickness direction of the dissecting device 200 agrees substantially with the aligning direction in which the dissecting device 200 and the great saphenous vein 1000 are aligned. In this operation, the dissecting device 200 is inserted between the fat 1200 and the skin 1400 (between the tissues having different properties), and the skin 1400 and the fat 1200 are dissected from each other in the thickness direction of the dissecting device 200 (in the aligning direction in which the dissecting device 200 and the great saphenous vein 1000 are aligned). Such an area is an area where dissection can be achieved particularly easily, so that this operation can be carried out more smoothly and accurately. The dissecting device 200 thus dissects tissue in a direction along the longitudinal extent of the vein.

Figure 4B:
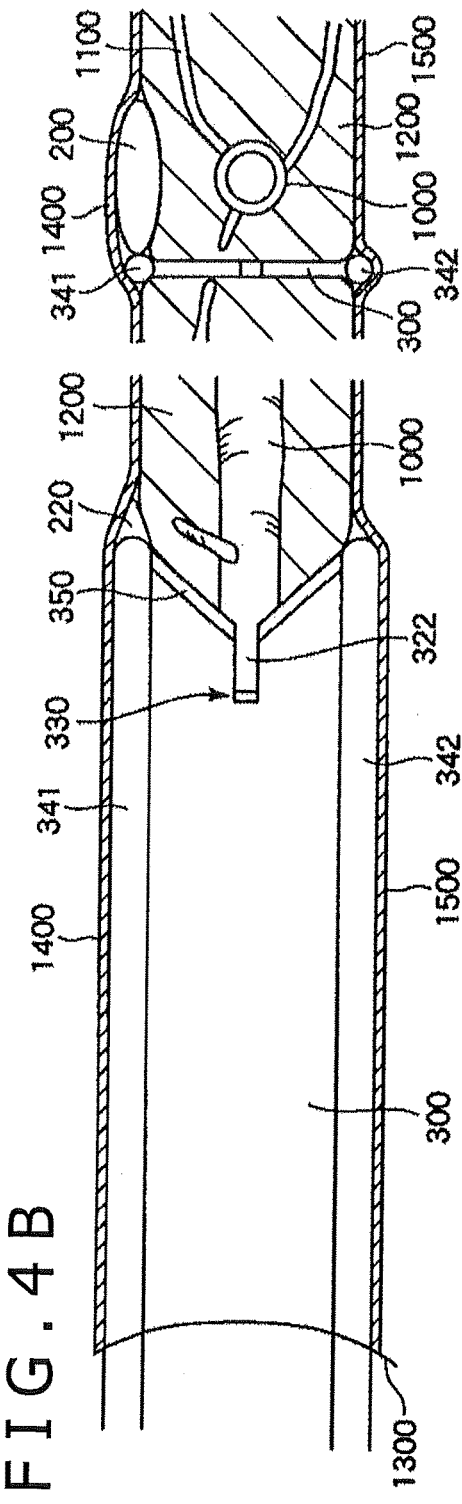

Subsequently, the cutting device 300 is prepared, and the connection section 381 is connected to the rail 231 of the dissecting device 200. Then, the state of the dissecting device 200 is aligned on the upper side of the great saphenous vein 1000, the cutting device 300 is inserted into and moved in the living body while guiding the cutting device 300 with the dissecting device 200 as shown in FIG. 4B. In this case, the cutting device 300 is moved forward while dissecting the skin 1400 from the fat 1200 by the protection section 341, and while dissecting the fascia 1500 from the fat 1200 by the protection section 342. Furthermore, the cutting device 300 cuts the fat 1200 present on the one lateral side of the great saphenous vein 1000 by the cutting edge section 350 in the left-right direction (in the aligning direction in which the cutting device 300 and the great saphenous vein 1000 are aligned), and, concurrently, cuts and stanches the branch vessel 1100 by the treating section 330.

Here, since the width W1 of the dissecting device 200 is greater than the outside diameter of the great saphenous vein 1000 as aforementioned, the cutting device 300 can be pushed forward along the great saphenous vein 1000 while keeping the cutting device 300 laterally spaced from the great saphenous vein 1000, as shown in FIG. 4B, so that the great saphenous vein 1000 can be prevented from being damaged during this operation. In addition, since the protection sections 341 and 342 are rounded, the possibility of damaging the skin 1400 or the fascia 1500 by contact with the cutting device 300 is lowered.

Next, the cutting device 300 is drawn out, and the connection section 382 of the cutting device 300 thus drawn out is connected to the rail 232 of the dissecting device 200. Then, the cutting device 300 is inserted again into the living body while guiding the cutting device 300 with the dissecting device 200, to dispose the cutting device 300 on the other lateral side of the great saphenous vein 1000, as shown in FIG. 5A.

Subsequently, the dissecting device 200 is drawn out, and the rail 232 of the dissecting device 200 thus drawn out is connected to the connection section 384 of the cutting device 300. Then, the dissecting device 200 is inserted again into the living body while guiding the dissecting device 200 with the cutting device 300, to dispose the dissecting device 200 on the lower side (the fascia 1500 side (bone side)) of the great saphenous vein 1000, as shown in FIG. 5B. In this operation, the dissecting device 200 is inserted between the fat 1200 and the fascia 1500 (inserted into the boundary between the tissues having different properties), and the fat 1200 and the fascia 1500 are dissected from each other in the thickness direction of the dissecting device 200. Such an area is an area where dissection can be particularly easily achieved, so that this operation can be carried out more smoothly and accurately.

By the above-mentioned operations, the fat 1200 surrounding the great saphenous vein 1000 is dissected over the entire perimeter of the vein, and the great saphenous vein 1000 is dissected in the state of being covered with the surrounding fat 1200. The thickness of the fat 1200 dissected together with the great saphenous vein 1000 and located in the surroundings of the great saphenous vein 1000 is not particularly limited. It is preferable, however, that the thickness is about 0.1 mm to 10 mm, more preferably about 1 mm to 8 mm, and further preferably about 3 mm to 5 mm.

Second Step

Next, both ends of that part of the great saphenous vein 1000 which is to be harvested are ligated and then cut.

Third Step

Subsequently, the great saphenous vein 1000 is extracted in the state of being covered with the surrounding fat 1200, to the outside of the living body via the incision 1300.

By the first to third steps as above-mentioned, the great saphenous vein 1000 can be harvested while the great saphenous vein is in the state of being covered with the surrounding fat 1200. In such a method, while using the dissecting device 200 for treating a part which is rather easy to dissect so as to reduce such damages as bleeding and while using the cutting device 300 for treating the fat which is difficult to dissect, the great saphenous vein 1000 can be harvested smoothly and with low invasion. In addition, since the first step can be carried out without cutting the great saphenous vein 1000, blood can be kept flowing through the great saphenous vein 1000 for a time as long as possible. Accordingly, the great saphenous vein 1000 is placed in an ischemic state for a shortened period of time, so that the great saphenous vein 1000 can be harvested with less damage.

Here, a great saphenous vein 1000 covered with fat 1200 constitutes a bypass vessel having a superior long-term patency rate, as compared with a great saphenous vein 1000 not covered with fat 1200. The reason is considered as follows. While the great saphenous vein 1000 is used as an artery bypass vessel, arteries are generally higher than veins in the blood pressure (the internal pressure exerted thereon by blood). When a great saphenous vein in an exposed state of being not covered with tissue is used as a bypass vessel, therefore, the great saphenous vein cannot endure the blood pressure and is therefore expanded by the blood pressure, resulting in lowered blood flow. In addition, thickening of blood vessel wall occurs in the process of remodeling (structural alteration) or in the process of recovery from damage to tissue. Such thickening of blood vessel wall is considered to influence the development of arterial sclerosis. From such a cause, the use of a great saphenous vein in the exposed state of being not covered with tissue as a bypass vessel would, in the long run, lead to vascular occlusion.

On the other hand, where the great saphenous vein 1000 is covered with fat 1200, expansion of the great saphenous vein 1000 is restrained by the fat 1200, and bending and the like of the great saphenous vein 1000 are also restrained. Therefore, the lowering in blood flow as above-mentioned can be inhibited. In addition, the covering with the fat 1200 reduces damages to the great saphenous vein 1000, specifically, damages to endotheliocytes, smooth muscles, nutrient vessels (capillary plexus), etc. Therefore, the aforementioned thickening of blood vessel walls can be restrained. For these reasons, the use of the great saphenous vein 1000 covered with the fat 1200 as a bypass vessel enables an excellent long-term patency rate. Especially, in this embodiment, nutrient vessels are left at the blood vessel walls of the great saphenous vein 1000 and in the fat 1200. For this reason, nutrients are supplied to the great saphenous vein 1000 serving as the bypass vessel, even after the bypass grafting. This is considered to be the reason why the aforementioned effect is enhanced.

While this embodiment has been described, the configuration of the blood vessel dissecting device 100 is not limited to the configuration in this embodiment. For example, the rails 231 and 232 may be omitted from the dissecting device 200, and the connection sections 381 to 384 may be omitted from the cutting device 300. In this case, for example, it may be sufficient to insert the cutting device 300 into a living body along the dissecting device 200 which is inserted into the living body earlier. Alternatively, it may be sufficient to insert the dissecting device 200 into a living body along the cutting device 300 which is inserted into the living body earlier.

The cutting device 300 is not specifically restricted insofar as it can cut the fat 1200. For instance, a configuration may be adopted in which the fat 1200 is cut by something like a pair of scissors.

The blood vessel dissecting method is not limited to the procedure adopted in this embodiment. For instance, the order of insertion of the dissecting device 200 and the cutting device 300 is not specifically restricted, and any of left, right, upper and lower portions of the great saphenous vein 1000 may be dissected first. For instance, a procedure may be adopted in which, first, upper and lower sides of the great saphenous vein 1000 are dissected by use of the dissecting device 200, and, then, left and right sides of the great saphenous vein 1000 are dissected by use of the cutting device 300. On the other hand, left and right sides of the great saphenous vein 1000 may first be dissected by use of the cutting device 300, and, then, upper and lower sides of the great saphenous vein 1000 may be dissected by use of the dissecting device 200.

While one dissecting device 200 and one cutting device 300 are used in this embodiment, two dissecting devices 200 and two cutting devices 300 may be used. In this case, for example, a procedure may be adopted wherein, first, a first dissecting device 200 is disposed on the upper side of the great saphenous vein 1000, next a first cutting device 300 is disposed on one of left and right sides of the great saphenous vein 1000, then a second cutting device 300 is disposed on the other of the left and right sides of the great saphenous vein 1000, and a second dissecting device 200 is disposed on the lower side of the great saphenous vein 1000. Such a procedure eliminates the need to draw out the dissecting device 200 and the cutting device 300 in the course of the procedure, so that the aforementioned procedure can be carried out smoothly.

While the dissecting device 200 is inserted between the fat 1200 and the skin 1400 and between the fat 1200 and the fascia 1500 in this embodiment, the insertion position of the dissecting device 200 is not particularly limited. For instance, the dissecting device 200 may be inserted between tissues having different properties, such as between the fat 1200 and a blood vessel (other than the great saphenous vein 1000), between the fat 1200 and a bone, between the fascia 1500 and a bone, or the like. Further, the insertion between tissues having different properties (insertion into the boundary between tissues having different properties, insertion into tissue between tissues having different properties, or the like) is not restrictive; for example, the dissecting device 200 may be inserted into the fat 1200, thereby dissecting the fat 1200.

While fat is cut by the cutting device 300 in this embodiment, the tissue to be cut by the cutting device 300 is not limited to fat. For instance, tissue between a skin-fat boundary and a fat-muscle boundary, tissue between a skin-fat boundary and a fat-interosseous membrane boundary, connective tissue, tissue between a skin layer and a muscle layer, tissue between a skin layer and an interosseous membrane, branch vessels, and the like may also be cut by the cutting device 300.

While the dissecting device 200 is disposed spaced from the great saphenous vein 1000 so as not to contact the great saphenous vein 1000 in this embodiment, the dissecting device 200 may be disposed in contact with the great saphenous vein 1000. In other words, the dissecting device 200 may be inserted between the great saphenous vein 1000 and the fat 1200.

Second Embodiment

Figure 6:
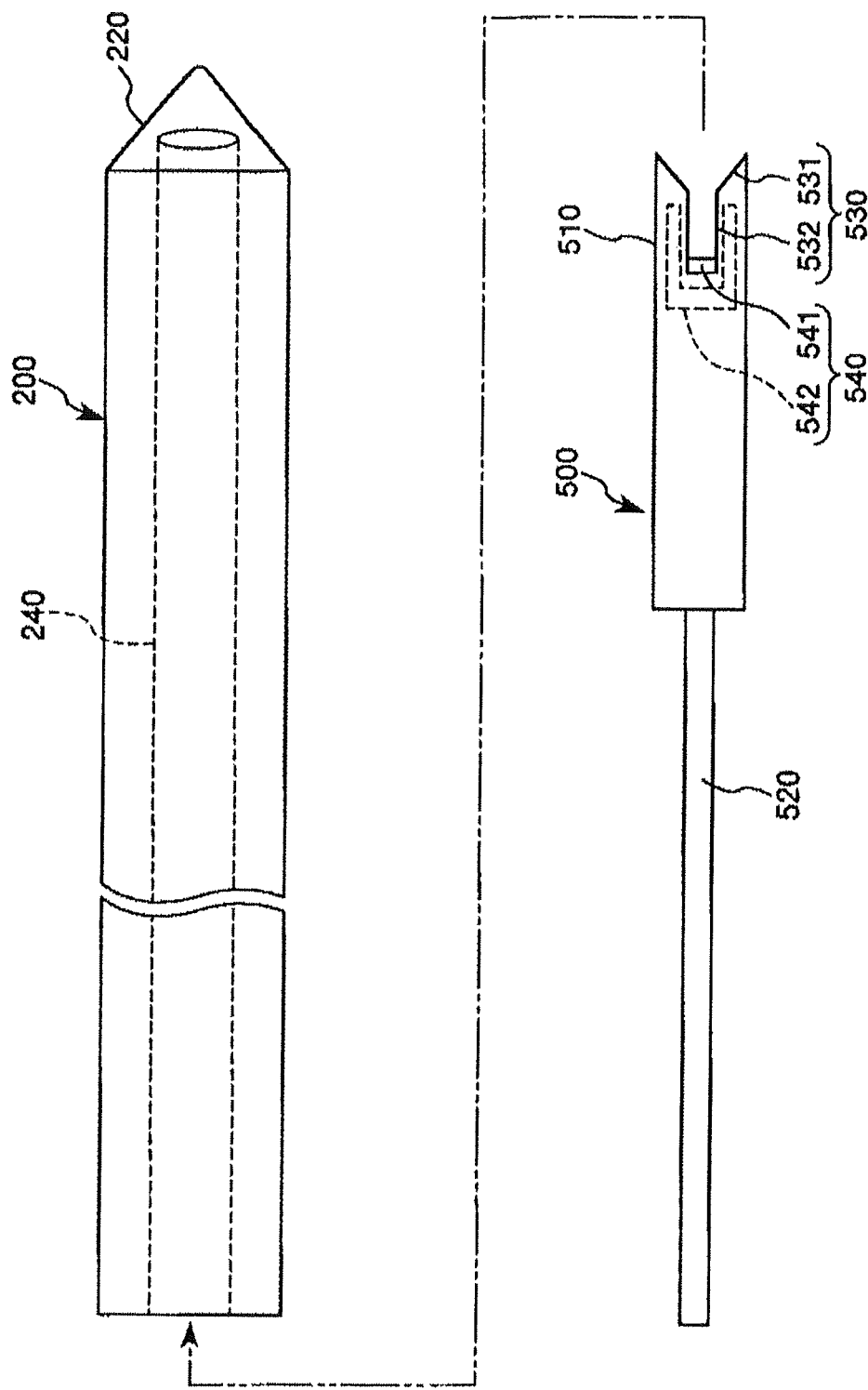
FIG. 6 illustrates a dissecting device and a blood vessel treating device forming a part of a blood vessel dissecting device according to a second embodiment of the present disclosure.
Figure 7A:
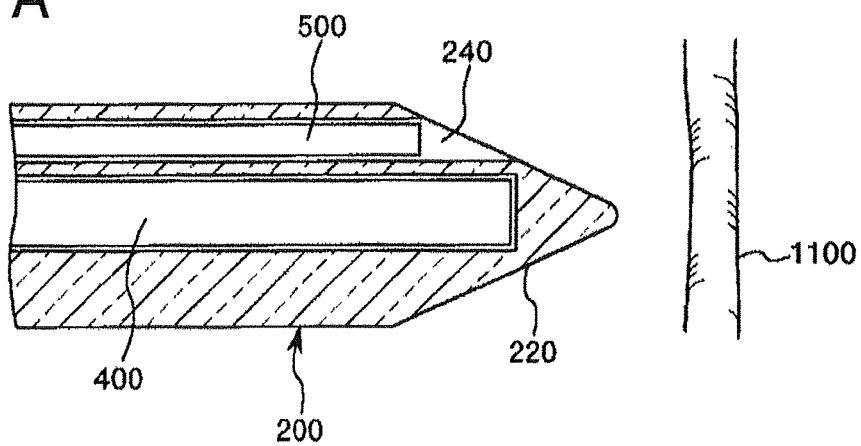
FIGS. 7A to 7C are views explaining a blood vessel dissecting method carried out using the blood vessel dissecting device shown in FIG. 6.
Figure 7B:
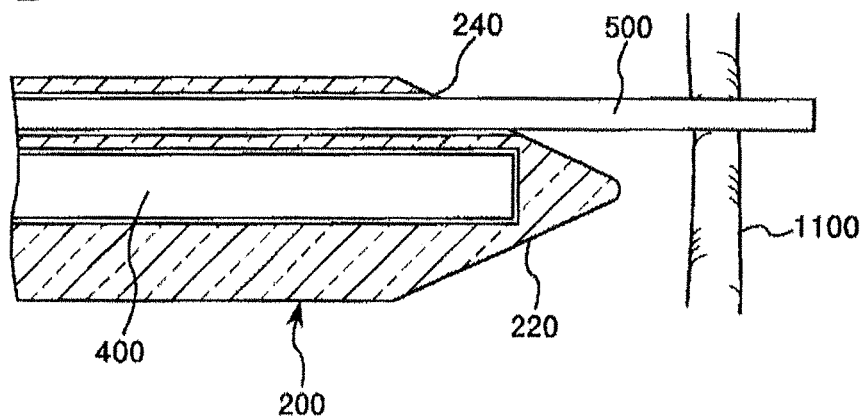
Figure 7C:
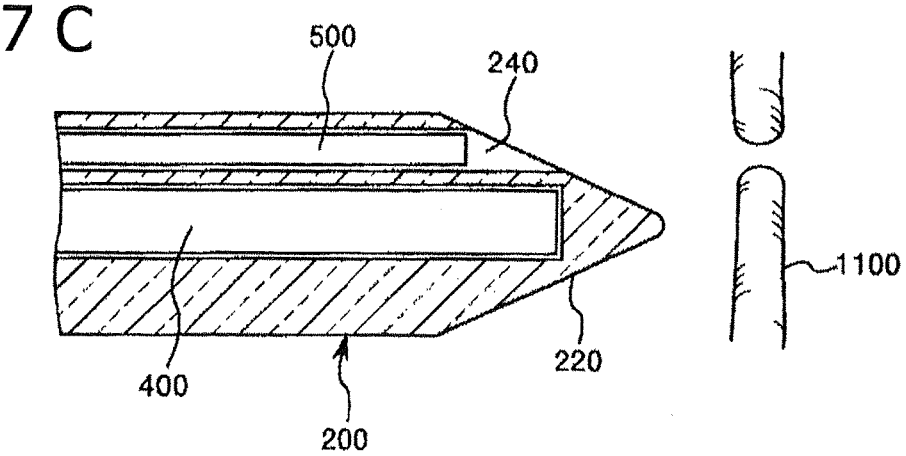

FIGS. 6-7C illustrate a second embodiment of a blood vessel dissecting device and a blood vessel dissecting method representing another example of the disclosure here.

Referring to these figures, the second embodiment will be described below. The following description will primarily describe differences associated with this embodiment relative to the aforementioned embodiment, and a detailed description of features which are the similar to features in the first embodiment will not be repeated.

This embodiment is the same as the first embodiment described above, except mainly that the blood vessel dissecting device in this embodiment further includes a blood vessel treating device used together with the dissecting device.

Blood Vessel Dissecting Device

A blood vessel dissecting device 100 in this embodiment includes a dissecting device 200, a cutting device 300, and a blood vessel treating device 500. Since the cutting device 300 is configured in the same manner as in the cutting device 300 in the first embodiment, the following detailed description will primarily focus on the dissecting device 200 and the blood vessel treating device 500.

Dissecting Device

The dissecting device 200 possesses the same configuration as described above in the first embodiment. In addition, the dissecting device 200 in this embodiment has a passing hole 240 in which the blood vessel treating device 500 is inserted and passed, as shown in FIG. 6. The passing hole 240 opens at the proximal end and a dissecting section 220 of the dissecting device 200. The passing hole 220 is thus a through hole open at both ends. The blood vessel treating device 500 can be inserted into the dissecting device 200 via the proximal-side opening, and can protrude from (distally beyond) the distal end of the dissecting device 200 via the distal-side opening.

Blood Vessel Treating Device

As shown in FIG. 6, the blood vessel treating device 500 includes a plate-shaped main body section 510, and a bar-shaped operating section 520 connected to the proximal end of the main body section 510. The main body section 510 has a groove portion 530 opening at a distal portion of the main body section 510. The groove portion 530 includes a tapered blood vessel guide groove section 531 having a width gradually decreasing toward the distal side, and a straight blood vessel treating groove section 532 which is located on the proximal side of the blood vessel guide groove section 531 and is substantially constant in width. The blood vessel guide groove section 531 is a groove section for guiding a branch vessel 1100 into the blood vessel treating groove section 532. On the other hand, the blood vessel treating groove section 532 is a groove section for cutting and stanching the branch vessel 1100 guided by the blood vessel guide groove section 531. The blood vessel treating groove section 532 is provided with a treating section 540 adapted to cut and stanch a branch vessel. The treating section 540 has a bipolar structure including a pair of electrodes 541 and 542 configured to generate an electric field inside the blood vessel treating groove section 532. The configuration of the treating section 540 is the same as that of the treating section 330 described above in the first section, and, therefore, a detailed description of the treating section 330 is not repeated here.

Blood Vessel Dissecting Method

In a first step, the dissecting device 200 is inserted into a living body. When a branch vessel 1100 appears on the forward side of the dissecting device 200, as depicted in FIG. 7A, the blood vessel treating device 500 is protruded from (extended distally beyond) the distal-side opening of the passing hole 240, as shown in FIG. 7B, and the branch vessel 1100 is cut and stanched by the treating section 540. Then, the blood vessel treating device 500 is retracted into the passing hole 240, as shown in FIG. 7C, and the dissecting device 200 is moved forward again. When such a procedure is followed, cutting of the branch vessel 1100 by the dissecting device 200 can be effectively prevented.

The blood vessel treating device 500 is not specifically restricted so long as it can treat the branch vessel 1100. For instance, the blood vessel treating device 500 may be one with a monopolar structure, such as an electrosurgical knife, or a pair of scissors may be used. In the case where a pair of scissors is used, a ligation device may be used jointly.

By the second embodiment described above, also, the same or equivalent effects to those of the aforementioned first embodiment can be produced.

Third Embodiment

Figure 8:
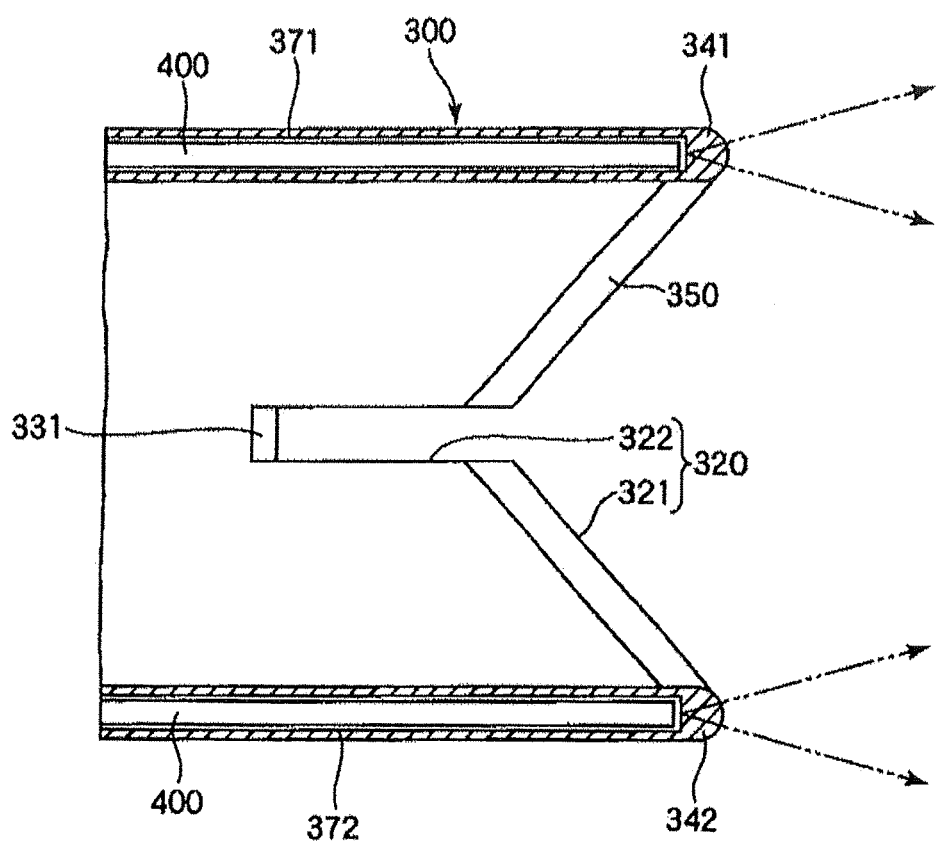
FIG. 8 is a partial cross-sectional view showing a cutting device forming a part of a blood vessel dissecting device according to a third embodiment of the present disclosure.

FIG. 8 illustrates a cutting device forming a part of a blood vessel dissecting device according to a third embodiment of the present disclosure.

Referring to this figure, the third embodiment will be described below. The description below will primarily focus on differences between this third embodiment and the embodiments described above. A detailed description of features and aspects of this third embodiment that are the same as those described above will not be repeated. This embodiment is the same as the first embodiment described above, except mainly that an imaging device can be inserted or provided in a cutting device.

Cutting Device

As shown in FIG. 8, a cutting device 300 in this embodiment has insertion holes 371 and 372 which are formed inside protection sections 341 and 342 and are open at proximal ends. Into the insertion holes 371 and 372 can be inserted imaging devices 400. In addition, at least distal portions of the protection sections 341 and 342 are substantially colorless and transparent and are light-transmitting. With the imaging devices 400 inserted in the insertion holes 371 and 372, therefore, the forward side of the cutting device 300 (particularly, a boundary area between fat 1200 and skin 1400, and a boundary area between fat 1200 and fascia 1500) can be observed by the imaging devices 400 through the protection sections 341 and 342. Consequently, the cutting device 300 can be inserted into a living body smoothly and accurately.

While the distal portions of the protection sections 341 and 342 are substantially colorless and transparent in this embodiment, these portions are not limited to being colorless and transparent insofar as they are light-transmitting; thus, the distal portions may be colored in red, blue, green or the like. While the protection sections 341 and 342 of the cutting device 300 in this embodiment are formed therein with the insertion holes such that two imaging devices 400 can be simultaneously inserted therein, the number of the insertion holes is not limited to two. For example, only one insertion hole may be provided. The layout of the insertion holes is also not particularly limited. In addition, a configuration may be adopted wherein the insertion holes are omitted and, for example, an imaging device 400 can be fixed on the outside of the cutting device 300.

By the third embodiment described above, also, the same or equivalent effects to those of the aforementioned first embodiment can be produced.

Fourth Embodiment

Figure 9A:
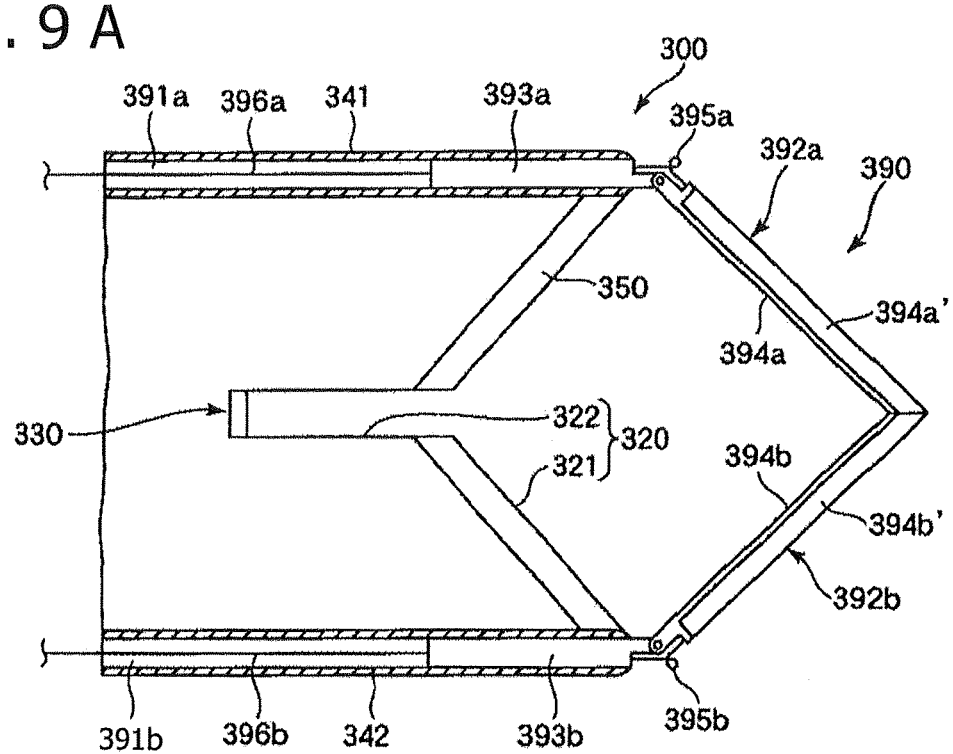
FIGS. 9A and 9B are partial cross-sectional views showing a cutting device forming a part of a blood vessel dissecting device according to a fourth embodiment of the present disclosure.
Figure 9B:
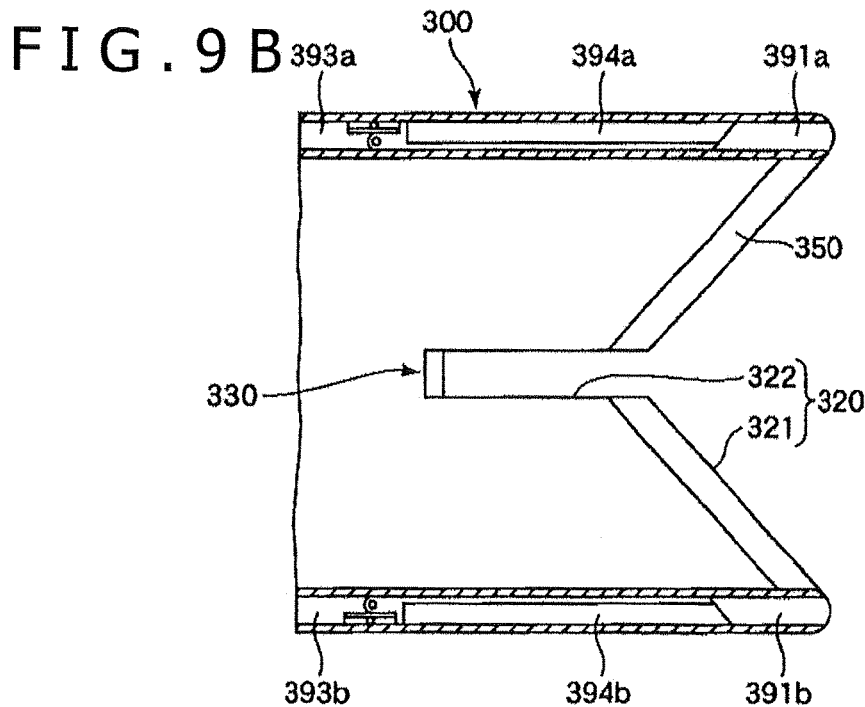

FIGS. 9A and 9B illustrate a cutting device forming a part of a blood vessel dissecting device according to a fourth embodiment of the present disclosure.

Referring to these figures, the fourth embodiment will be described below. The following description will primarily focus on differences between this fourth embodiment and embodiments described above. A detailed description of features and aspects of this fourth embodiment that are the same as those described above will not be repeated.

This embodiment is the same as the first embodiment described above, except mainly for differences in the configuration of cutting device.

Cutting Device

As shown in FIGS. 9A and 9B, a cutting device 300 in this embodiment has an insertion guide section 390 for facilitating the insertion of the cutting device 300 into a living body.

The insertion guide section 390 has accommodation holes 391a and 391b which are formed along and inside protection sections 341 and 342 and have distal ends opening in the protection sections 341 and 342. Furthermore, the insertion guide section 390 includes a first guide mechanism 392a disposed in the accommodation hole 391a, and a second guide mechanism 392b disposed in the accommodation hole 391b. The first guide mechanism 392a includes a proximal portion 393a disposed slidably in the accommodation hole 391a, a distal portion 394a located on the distal side of the proximal portion 393a and connected to and turnable relative to the proximal portion 393a, a spring member (biasing section) 395a for biasing the distal portion 394a toward the center axis side with reference to the proximal portion 393a, and a cord (operating section) 396a connected to the proximal portion 393a. Similarly, the second guide mechanism 392b includes a proximal portion 393b disposed slidably in the accommodation hole 391b, a distal portion 394b located on the distal side of the proximal portion 393b and connected to and turnable relative to the proximal portion 393b, a spring member 395b for biasing the distal portion 394b toward the center axis side with reference to the proximal portion 393b, and a cord 396b connected to the proximal portion 393b.

In the insertion guide section 390 as above, when the distal portions 394a and 394b protrude from (extend distally outside of) the accommodation holes 391a and 391b, the distal portions 394a and 394b are tilted toward the center axis side by the biasing forces of the spring members 395a and 395b so that their distal ends come in contact with each other. As a result, the groove section 320 is closed, and a distal portion of the cutting device 300 is deformed into a tapered shape. Accordingly, it becomes easier for the cutting device 300 to be inserted into a living body via an incision 1300. In addition, the distal portions 394a and 394b have cutting edge sections 394a' and 394b' directed toward the forward side when the distal portions 394a and 394b are tilted to the center axis side. This helps ensure easier insertion of the cutting device 300 into the living body through the incision 1300. On the other hand, when the cords 396a and 396b are pulled proximally, the distal portions 394a and 394b are retracted into the accommodation holes 391a and 391b so that the groove section 320 and a treating section 330 appear, as depicted in FIG. 9B.

When the cutting device 300 having the insertion guide section 390 as above is inserted, in the state shown in FIG. 9A, into a living body, the inserting operation can be carried out more smoothly. Thereafter, the cutting device 300 is moved forward within the living body in the state shown in FIG. 9B, whereby cutting of fat 1200 and a treatment (cutting and stanching) of a branch vessel 1100 can be performed in the same manner as in the aforementioned first embodiment.

By the fourth embodiment described above, also, the same or equivalent effects to those of the aforementioned first embodiment can be produced.

Fifth Embodiment

Figure 10A:
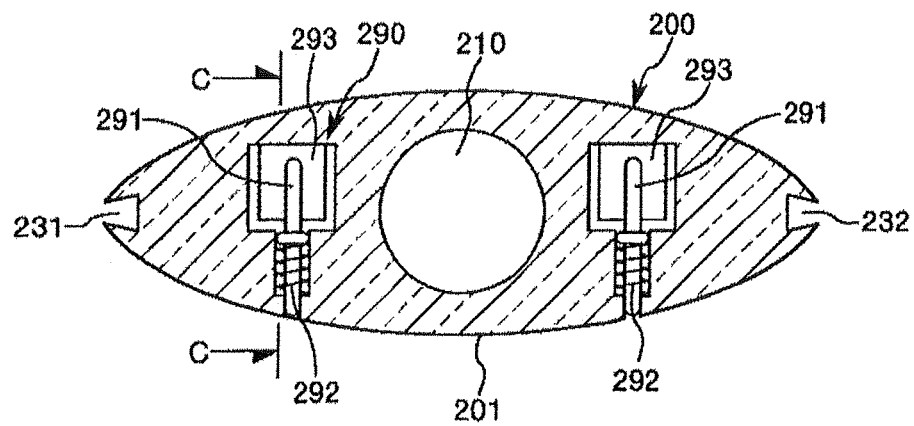
FIGS. 10A to 10C are cross-sectional views showing a dissecting device forming a part of a blood vessel dissecting device according to a fifth embodiment of the present disclosure.
Figure 10B:
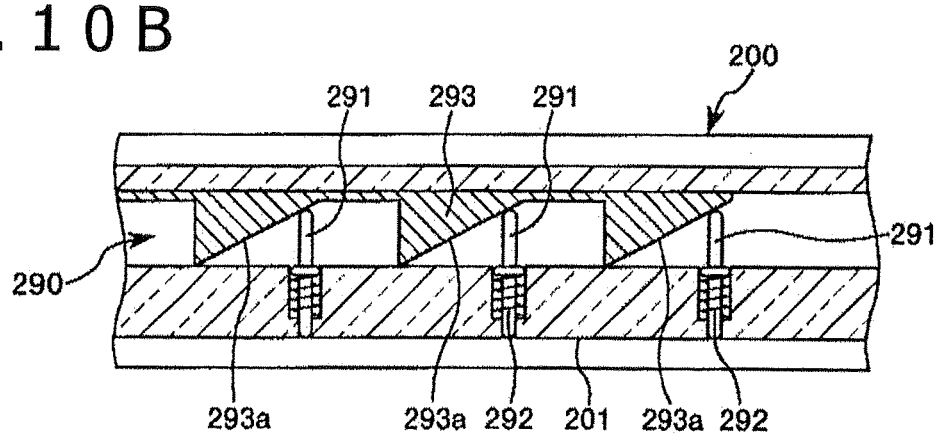
Figure 10C:
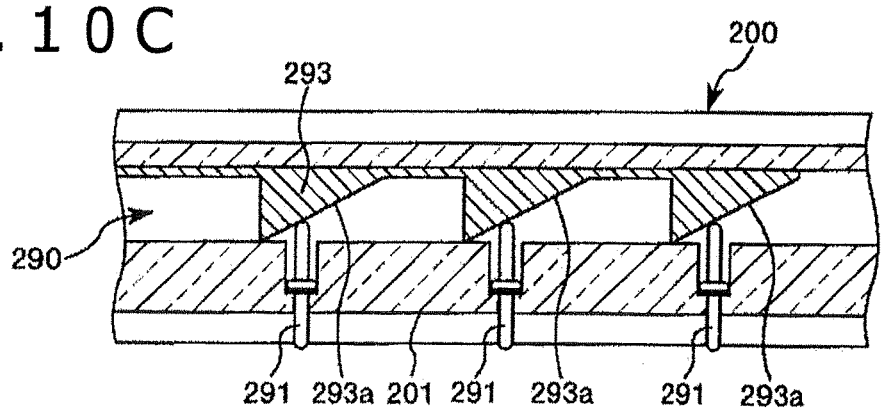
Figure 11:
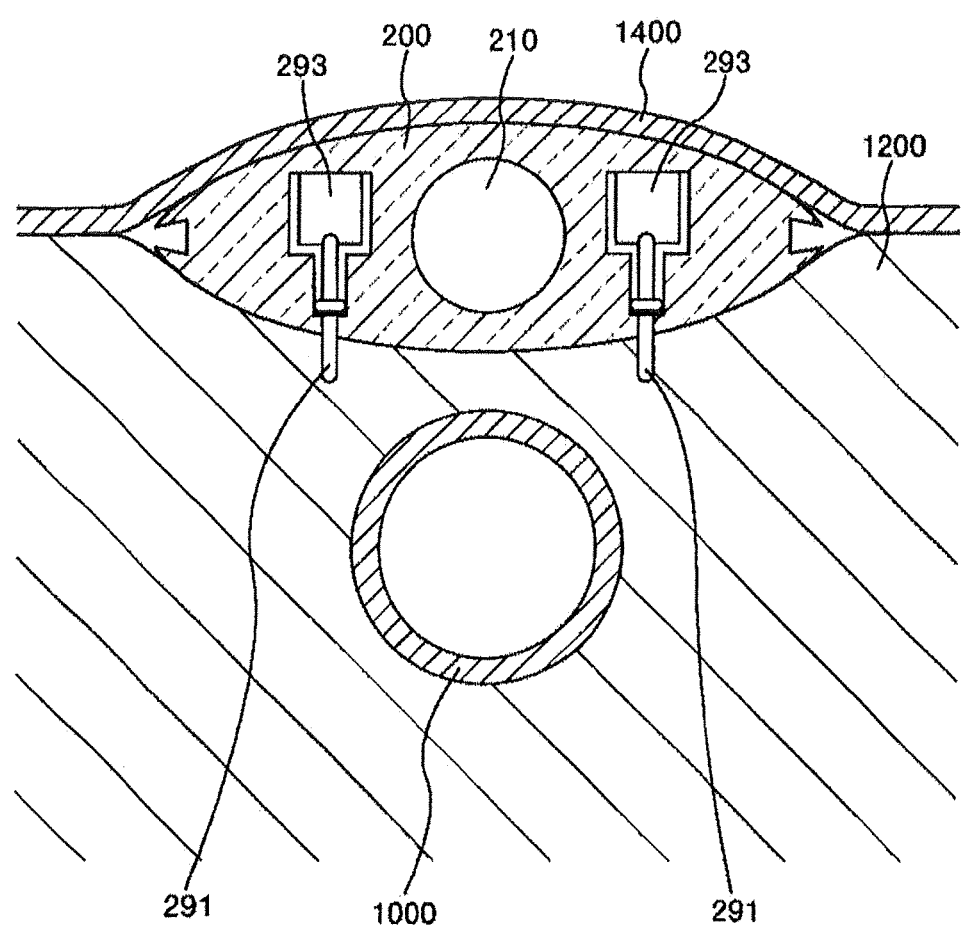
FIG. 11 is a cross-sectional view for explaining an effect of the dissecting device shown in FIGS. 10A to 10C.

FIGS. 10A to 11 illustrate a dissecting device forming a part of a blood vessel dissecting device according to a fifth embodiment of the present disclosure.

Referring to these figures, the fifth embodiment will be described below. In the following, the description will focus primarily on differences between this fifth embodiment and the embodiments described above. A detailed description of features and aspects of this fifth embodiment that are the same as those described above will not be repeated.

This embodiment is the same as the first embodiment described above, except mainly for differences in the configuration of the dissecting device.

Dissecting Device

As shown in FIGS. 10A to 10C, a dissecting device 200 in this embodiment has an anchoring mechanism 290 for reducing a slippage (displacement) of the dissecting device 200 in a living body. The anchoring mechanism 290 includes: a projection (anchoring section) 291 disposed and configured to project from and retract into the dissecting device 200; a spring member (biasing section) 292 for biasing the projection 291 toward the inside of the dissecting device 200; and an operating section 293 for operating (depressing) the projection 291. The projections 291 are arranged on both sides with respect to the width direction of the dissecting device 200, and are arranged plural in number in spaced-apart relation in along the axial direction of the dissecting device 200. Each of the projections 291 is biased toward the inside by the spring member 292, and, in the retracted state depicted in FIG. 10B, the projection 291 is retracted in the dissecting device 200. The operating section 293 is disposed inside the dissecting device 200 so as to be slidably moved in the axial direction. The operating section 293 has a contact surface 293a which is inclined against the axial direction and makes contact with the projection 291.

When the operating section 293 is slid toward the distal side, the projection 291 is depressed downward by the contact surface 293a, as shown in FIG. 10C, resulting in that the projection 291 protrudes from the surface (lower surface) of the dissecting device 200 to the exterior. When the operating section 293 is slid toward the proximal side starting from this condition, the biasing force of the spring member 292 causes the projection 291 to be again retracted into the dissecting device 200.

The dissecting device 200 having the anchoring mechanism 290 as above helps ensure that when the dissecting device 200 with the projections 291 in the retracted state is inserted into a living body and thereafter the projections 291 protrude to the side of a great saphenous vein 1000, the projections 291 bite into fat 1200, as shown in FIG. 11. As a result, slippage of the dissecting device 200 in relation to the great saphenous vein 1000 can be reduced, so that the dissecting device 200 can be maintained in an appropriate position during the intended technique. Accordingly, it is possible, for example, to guide the cutting device 300 more accurately.

The projections 291 are configured to protrude or project in the thickness direction of the dissecting device 200 from a surface 201 on one side with respect to the thickness direction, but the place and the direction of protrusion of each of the projections 291 are not restricted in this way. In addition, while the projection 291 is used as the anchoring section in this embodiment, the anchoring section is not limited to this; for example, a plate-shaped member may be used in place of the projection. While the projection 291 is protruded and retracted by use of the operating section 293 and the spring member 292 in this embodiment, the configuration for protrusion and retraction of the projection 291 is not restricted to this; for example, a drive source such as a motor may be used to electrically effect protrusion and retraction of the projection 291.

By the fifth embodiment described above, also, the same or equivalent effects to those of the first embodiment described above can be produced.

Sixth Embodiment

Figure 12A:
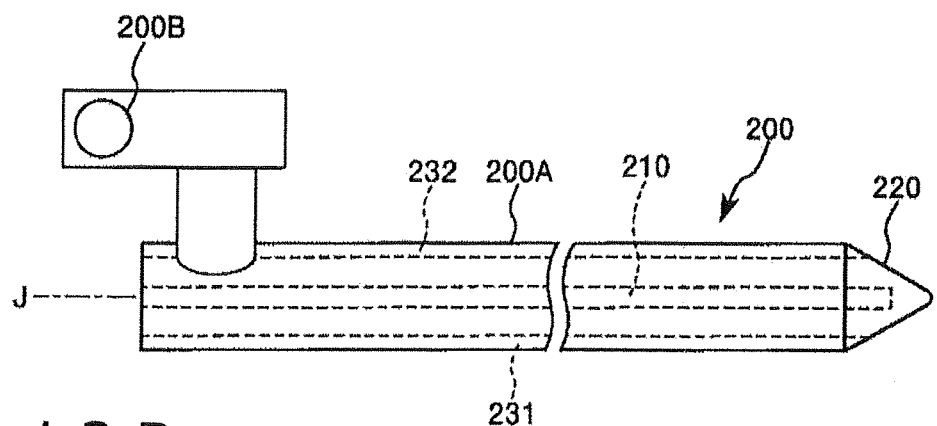
Figure 12B:
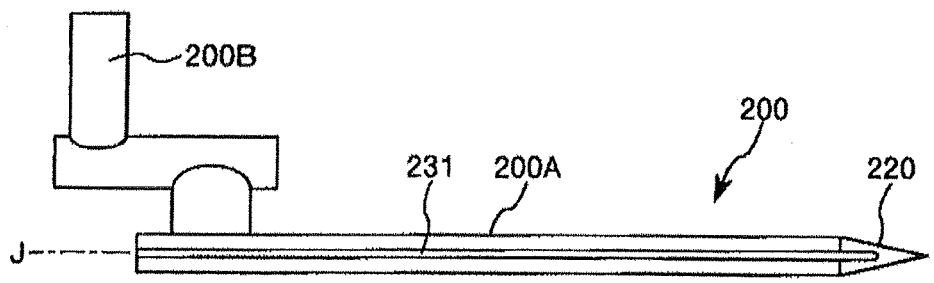
Figure 12C:
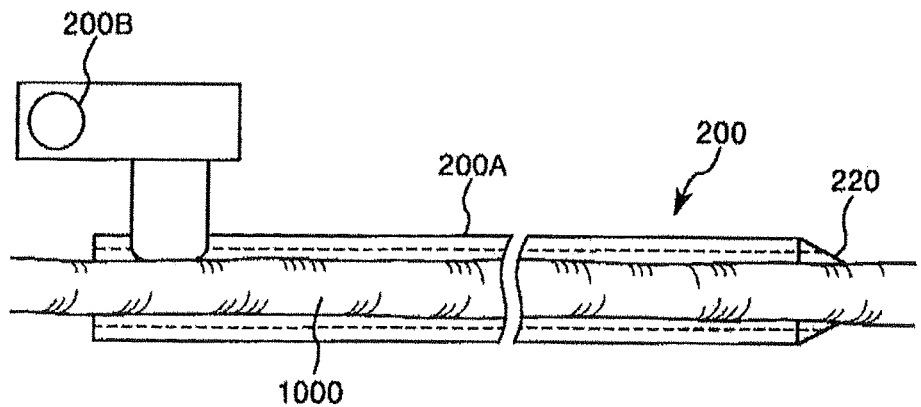

FIGS. 12A to 12C illustrate a dissecting device possessed by a blood vessel dissecting device according to a sixth embodiment of the present disclosure.

Referring to these figures, the sixth embodiment will be described below. In the following, the detailed description will primarily focus on differences between this embodiment and the embodiments described above. A detailed description of features and aspects of this sixth embodiment that are the same as those described above will not be repeated.

This embodiment is the same as the first embodiment described above, except mainly for differences in the configuration of dissecting device.
Dissecting Device As shown in FIGS. 12A and 12B, a dissecting device 200 in this embodiment includes: an insertion section 200A inserted into a living body; and an operating section (grip section) 200B located on the proximal side of the insertion section 200A and used for operating the insertion section 200A. The operating section 200B is shifted (deviated) in relation to the center axis J of the insertion section 200A, both in the thickness direction and in the width direction. In other words, the operating section 200B is offset from the center axis J of the insertion section 200A, both in the thickness direction and in the width direction.

The dissecting device 200 configured as above helps ensure easier disposition of the dissecting device 200 on the lower side (bone side) of a great saphenous vein 1000. To be more specific, since the operating section 200B is offset from the center axis J of the insertion section 200A, at the time of inserting the dissecting device 200 to the lower side of the great saphenous vein 1000, the operating section 200B does not overlap with (does not make contact with) the great saphenous vein 1000, as shown in FIG. 12C. Therefore, the dissecting device 200 can be more easily disposed along the great saphenous vein 1000.

By the sixth embodiment described above, also, the same or equivalent effects to those of the first embodiment described above can be produced.

Seventh Embodiment

Figure 13A:
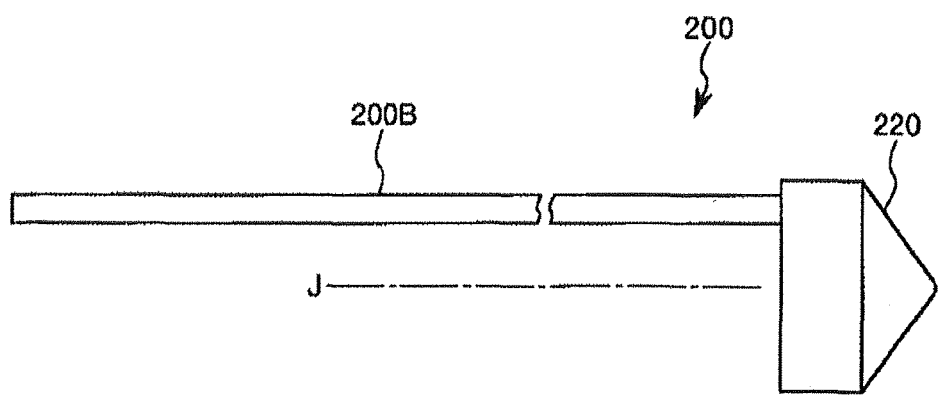
Figure 13B:
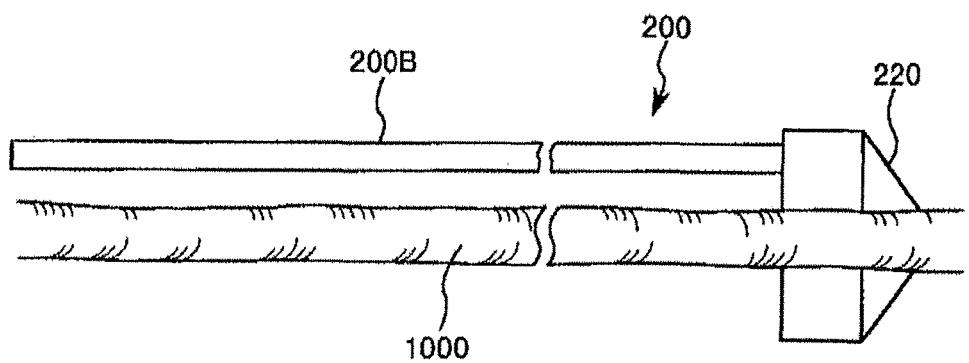

FIGS. 13A and 13B illustrate a dissecting device possessed by a blood vessel dissecting device according to a seventh embodiment of the present disclosure.

Referring to these figures, the seventh embodiment will be described below. The following detailed description will focus primarily on differences between this seventh embodiment and the embodiments described above. A detailed description of features and aspects of this seventh embodiment that are the same as those described above will not be repeated.

This embodiment is the same as the first embodiment described above, except mainly for differences in the configuration of dissecting device.
Dissecting Device As shown in FIG. 13A, a dissecting device 200 in this embodiment includes: a dissecting section 220; and an operating section 200B located on the proximal side of the dissecting section 220 and used to operate the dissecting section 220. The operating section 200B is disposed so that the operating section 200B is shifted (deviated) in the width direction in relation to the center axis J of the dissecting section 220. The dissecting device 200 configured in this way helps ensure that at the time of disposing the dissecting device 200 on the lower side (bone side) of a great saphenous vein 1000, the great saphenous vein 1000 and the operating section 200B do not overlap with each other, as shown in FIG. 13B. Therefore, it is easier to dispose the dissecting device 200 as desired.

By the seventh embodiment described above, also, the same or equivalent effects to those of the first embodiment described above can be produced.

Eighth Embodiment

Figure 14:
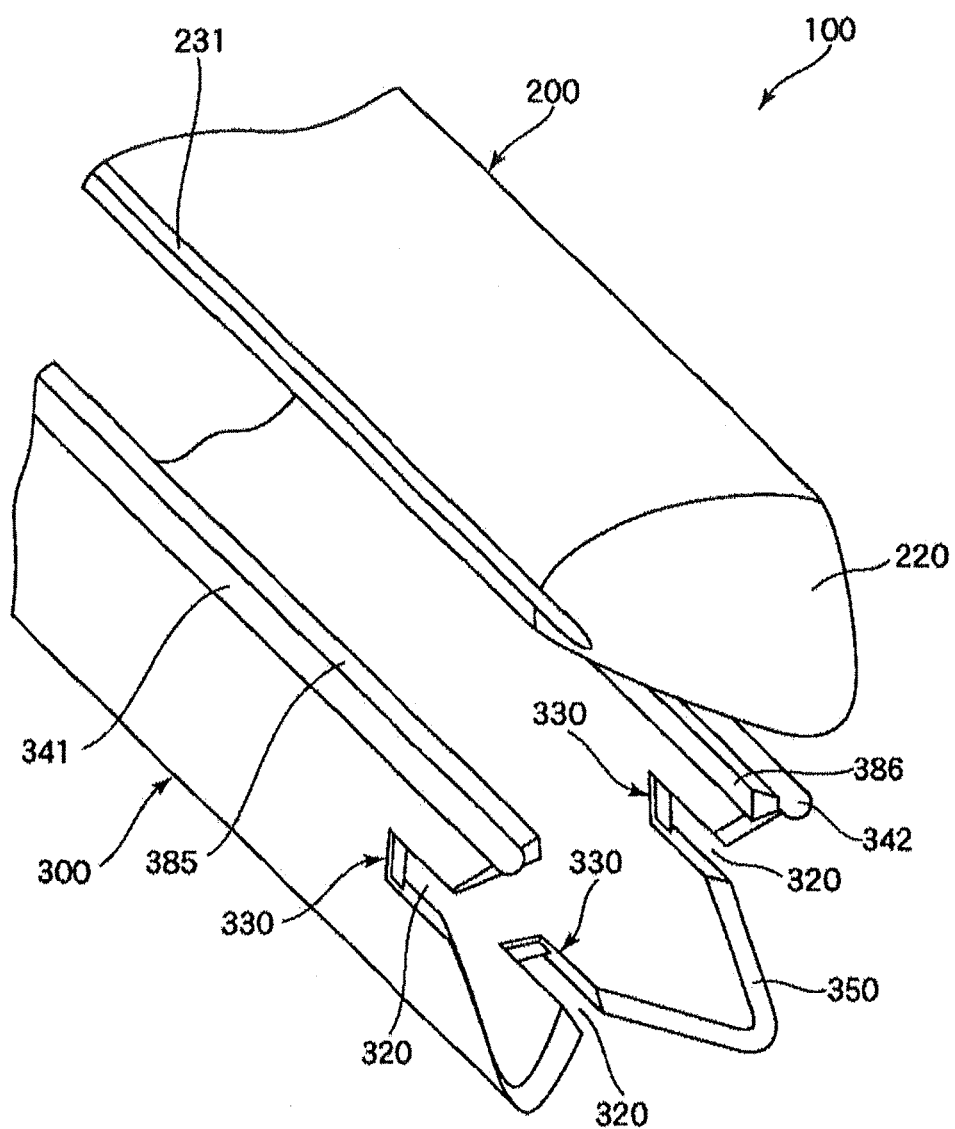
FIG. 14 is a perspective view of a blood vessel dissecting device according to an eighth embodiment of the present disclosure.

FIG. 14 is a perspective view of a blood vessel dissecting device according to an eighth embodiment of the present disclosure.

Referring to this figure, the eighth embodiment will be described below. The following detailed description will focus primarily on differences between this embodiment and the embodiments described above. A detailed description of features and aspects of this eighth embodiment that are the same as those described above will not be repeated.

This embodiment is the same as the aforementioned first embodiment, except mainly for differences in the configuration of cutting device.
Cutting Device As shown in FIG. 14, a cutting device 300 in this embodiment has a roughly C-shaped cross-section. A protection section 341 is disposed at one end portion with respect to the circumferential direction, and a protection section 342 is disposed at the other end portion with respect to the circumferential direction. The protection section 341 is provided with a connection section 385, in the form of a stretch of projection (or a rib or ridge), for connection with a rail 231 of a dissecting device 200. The protection section 342 is provided with a connection section 386, in the form of a stretch or length of projection (or a rib or ridge), for connection with the rail 232 of the dissecting device 200. In addition, groove sections 320 and treating sections 330 are disposed in pluralities along the circumferential direction. In the illustrated embodiment, the treating section 330 is positioned circumferentially between the groove sections 320.

An example of a manner of use of the cutting device 300 configured in this fashion is as follows. First, the dissecting device 200 is inserted into a living body (on the upper side or lower side of a great saphenous vein 1000). Next, the cutting device 300 is connected to the dissecting device 200, and the cutting device 300 is inserted into the living body while the cutting device 300 is guided by the dissecting device 200. As a result, the great saphenous vein 1000 is dissected over the entire range in the circumferential direction of the vein. This embodiment helps ensure that, for example as compared with the first embodiment, the first step can be carried out in a reduced number of procedures (steps).

By the eighth embodiment described above, also, the same or equivalent effects to those of the first embodiment described above can be produced.

Ninth Embodiment

Figure 15A:
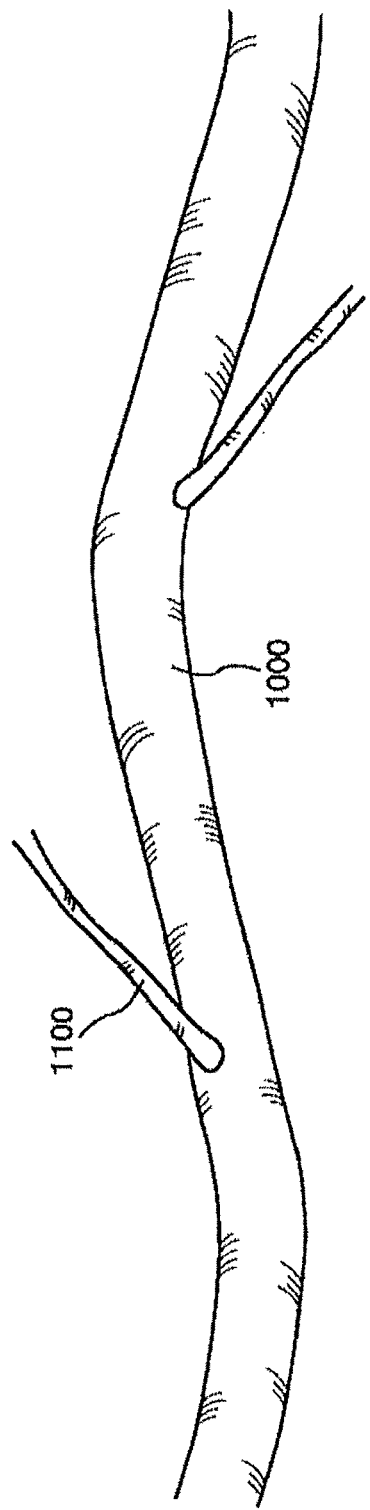
FIG. 15A illustrates a great saphenous vein.
Figure 15B:
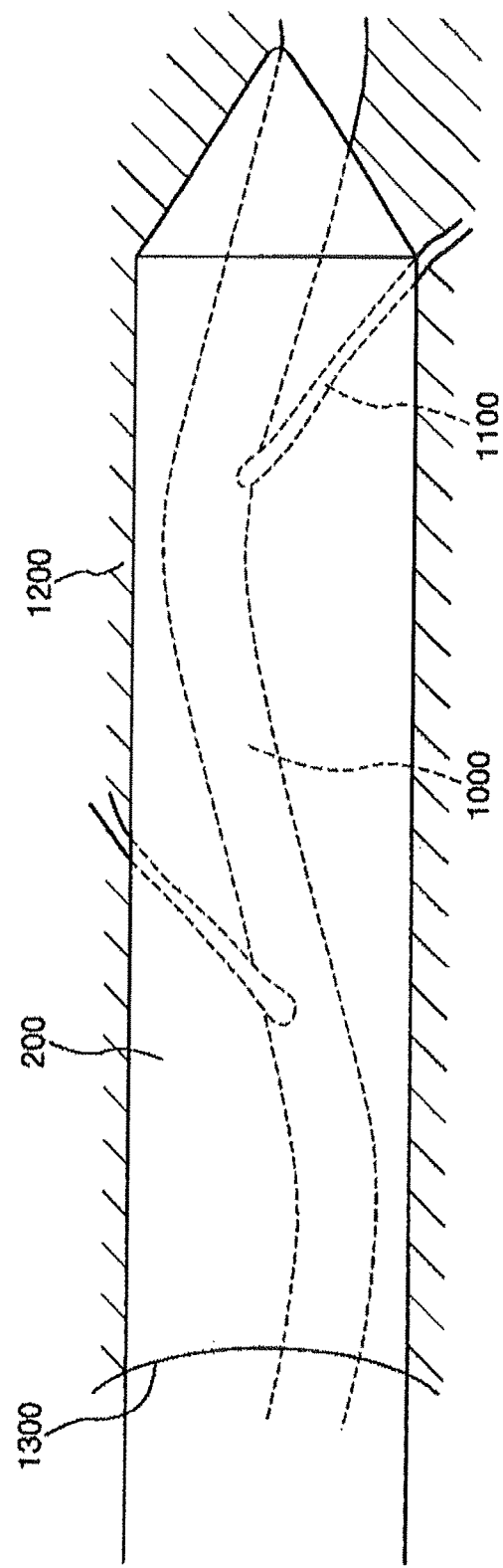
FIG. 15B is a plan view of a dissecting device forming a part of a blood vessel dissecting device according to a ninth embodiment of the present disclosure.

FIG. 15A illustrates a great saphenous vein, and FIG. 15B is a plan view of a dissecting device forming a part of a blood vessel dissecting device according to a ninth embodiment of the present disclosure.

Referring to these figures, the ninth embodiment will be described below. The following detailed description will focus primarily on differences between this ninth embodiment and the embodiments described above. A detailed description of features and aspects of this ninth embodiment that are the same as those described above will not be repeated.

This embodiment is the same as the first embodiment described above, except mainly for differences in the configuration of dissecting device.

As depicted in FIG. 15A, a great saphenous vein 1000 may not extend straight but may extend tortuously (in a somewhat meandering manner). In view of this, a dissecting device 200 in this embodiment is designed to be sufficiently large in width so that upon insertion into a living body, the dissecting device 200 overlaps the whole area of that portion of the great saphenous vein 1000 which is to be dissected. This helps ensure that, at the time of inserting a cutting device 300 along the dissecting device 200 after insertion of the dissecting device 200 into the living body, contact between the cutting device 300 and the great saphenous vein 1000 can be prevented from occurring. Therefore, damage to the great saphenous vein 1000 can be avoided or prevented. In addition, the dissection of the great saphenous vein 1000 in a state where the vein part to be dissected is entirely covered with fat 1200 can be achieved more reliably.

By the ninth embodiment described above, also, the same or equivalent effects to those of the first embodiment described above can be produced.

Tenth Embodiment

Figures 16A, 16B:
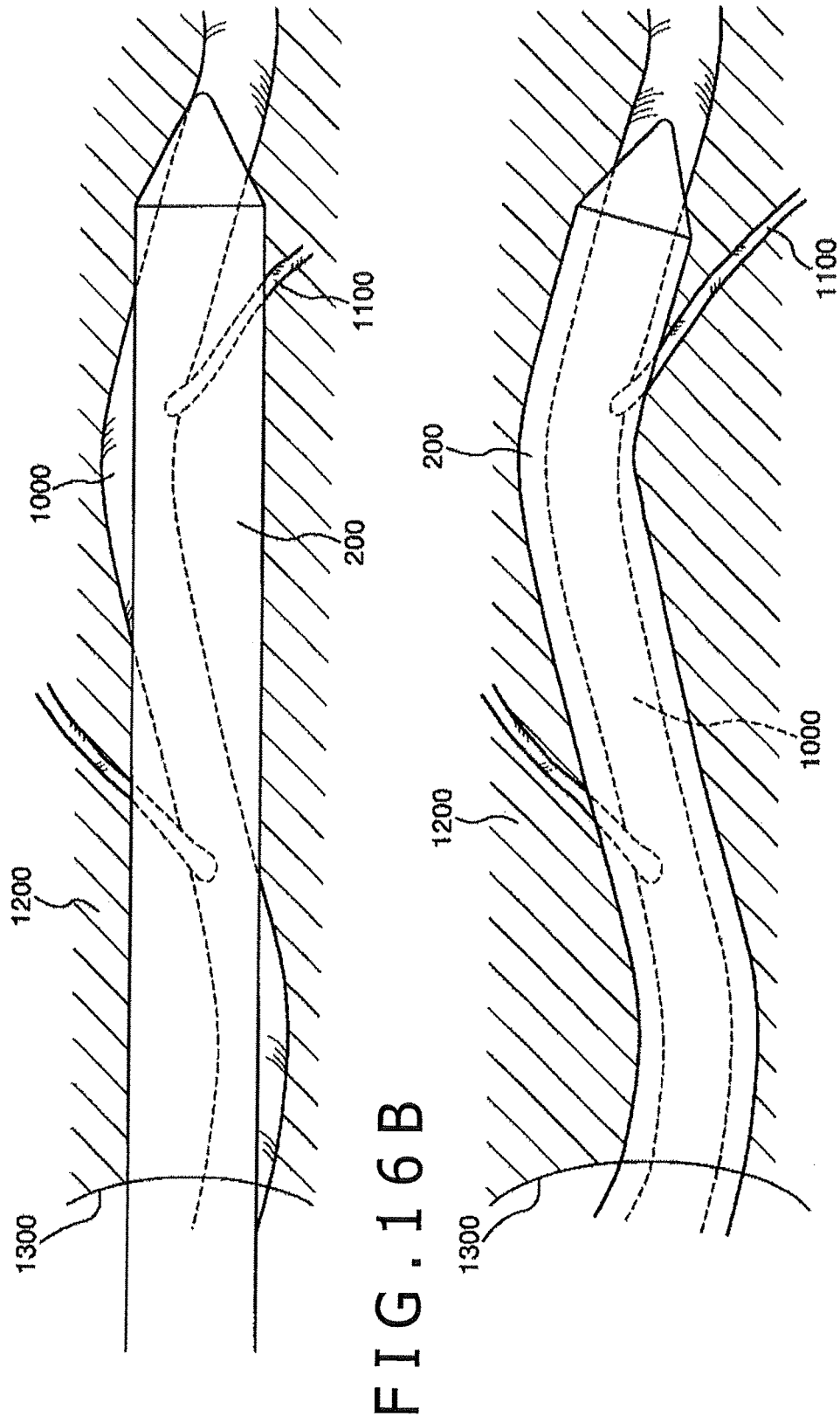
FIGS. 16A and 16B are plan views of a dissecting device forming a part of a blood vessel dissecting device according to a tenth embodiment of the present disclosure.

FIGS. 16A and 16B are plan views of a dissecting device forming a part of a blood vessel dissecting device according to a tenth embodiment of the present disclosure.

Referring to these figures, the tenth embodiment will be described below. The following detailed description will focus primarily on differences between this embodiment and the embodiments described above. A detailed description of features and aspects of this tenth embodiment that are the same as those described above will not be repeated.

This embodiment is the same as the first embodiment described above, except mainly for differences in the configuration of dissecting device.

A dissecting device 200 in this embodiment is deformable at least in the width direction of the dissecting device 220, and is configured to retain its deformed state. First, as shown in FIG. 16A, the dissecting device 200 set in a substantially straight form is inserted into a living body along a great saphenous vein 1000 to form an insertion hole, and then the dissecting device 200 is drawn out of the living body. The dissecting device 200 is deformed in conformity with the shape of the great saphenous vein 1000, and thereafter the deformed dissecting device 220 is inserted again into the insertion hole. By this procedure, the dissecting device 200 can be disposed in conformity with the tortuous state of the great saphenous vein 1000, as shown in FIG. 16B. At the time of inserting the cutting device 300 into the living body along the dissecting device 200, therefore, contact between the cutting device 300 and the great saphenous vein 1000 can be prevented from occurring, so that damage to the great saphenous vein 1000 can be avoided or prevented. In addition, the great saphenous vein 1000 can be dissected in a state of being entirely covered substantially evenly with fat 1200. Cutting-away of the fat 1200 in a surplus amount can also be restrained.

The tortuous state of the great saphenous vein 1000 can be grasped on the basis of images obtained, for example, by a diagnosis carried out using MRI (magnetic resonance imaging), CT (computed tomography) scan, ultrasound, infrared rays (near infrared rays), X-rays, an endoscope, or the like.

With the dissecting device 200 secured to the living body (a leg part of the patient), the insertion of the cutting device 300 can be carried out more smoothly. The method for securing the dissecting device 200 to the living body is not particularly limited. For example, there can be adopted a method wherein a fixture capable of being fixed by winding around a leg part is mounted onto the leg part, and the dissecting device 200 is secured to the fixture.

By the tenth embodiment described above, also, the same or equivalent effects to those of the first embodiment described above can be produced.

Eleventh Embodiment

FIGS. 17A and 17B are plan views of a dissecting device possessed by a blood vessel dissecting device according to an eleventh embodiment of the present disclosure.

Referring to these figures, the eleventh embodiment will be described below. The following detailed description will focus primarily on differences between this eleventh embodiment and the embodiments described above. A detailed description of features and aspects of this embodiment that are the same as those described above will not be repeated.

This embodiment is the same as the first embodiment described above, except mainly that the blood vessel dissecting device in this embodiment further includes a guide device.

A blood vessel dissecting device 100 in this embodiment includes a guide device 600 shown in FIG. 17A, in addition to a dissecting device 200 and a cutting device 300. The guide device 600 is designed in conformity to a preliminarily grasped shape of a great saphenous vein 1000. The guide device 600 is provided with rails 601 and 602 for guiding the cutting device 300; on the other hand, rails 231 and 232 are omitted from the dissecting device 200.

In using the blood vessel dissecting device 100 configured in this way, first, the dissecting device 200 is inserted into the living body along the great saphenous vein 1000 to form an insertion hole, and is drawn out of the living body. Next, the guide device 600 is inserted again into the insertion hole. As a result, the guide device 600 can be disposed in conformity with the tortuous state of the great saphenous vein 1000 as shown in FIG. 17B. Therefore, at the time of inserting the cutting device 300 into the living body along the guide device 600, contact between the cutting device 300 and the great saphenous vein 1000 can be prevented from occurring, so that damage to the great saphenous vein 1000 can be avoided or prevented. The great saphenous vein 1000 can be dissected in a state of being entirely covered substantially evenly with fat 1200. In addition, cutting-away of the fat 1200 in a surplus amount can be restrained.

By the eleventh embodiment described above, also, the same or equivalent effects to those of the first embodiment described above can be produced.

Twelfth Embodiment

Figure 18A:
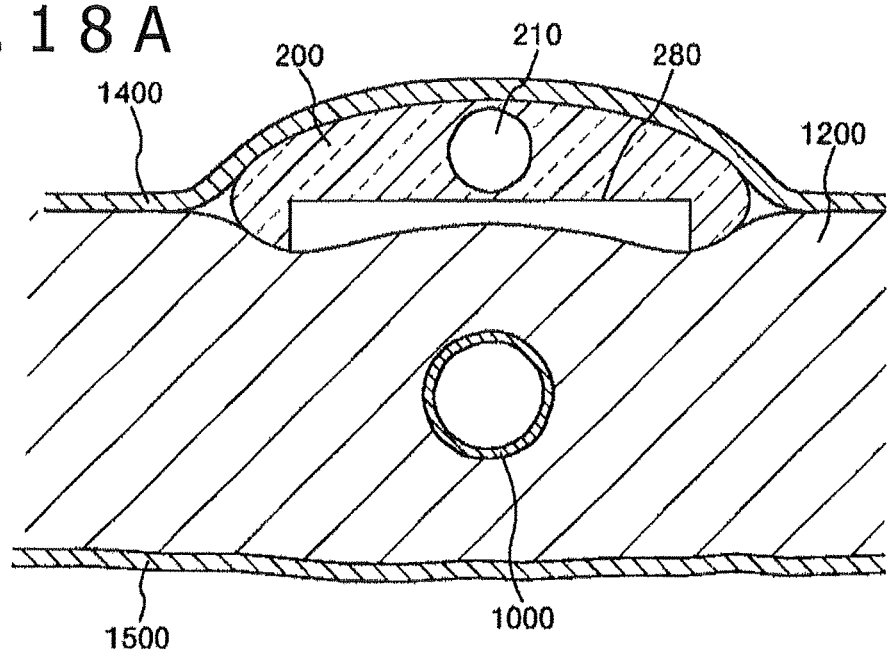
FIGS. 18A and 18B are cross-sectional views of a blood vessel dissecting device according to a twelfth embodiment of the present disclosure.
Figure 18B:
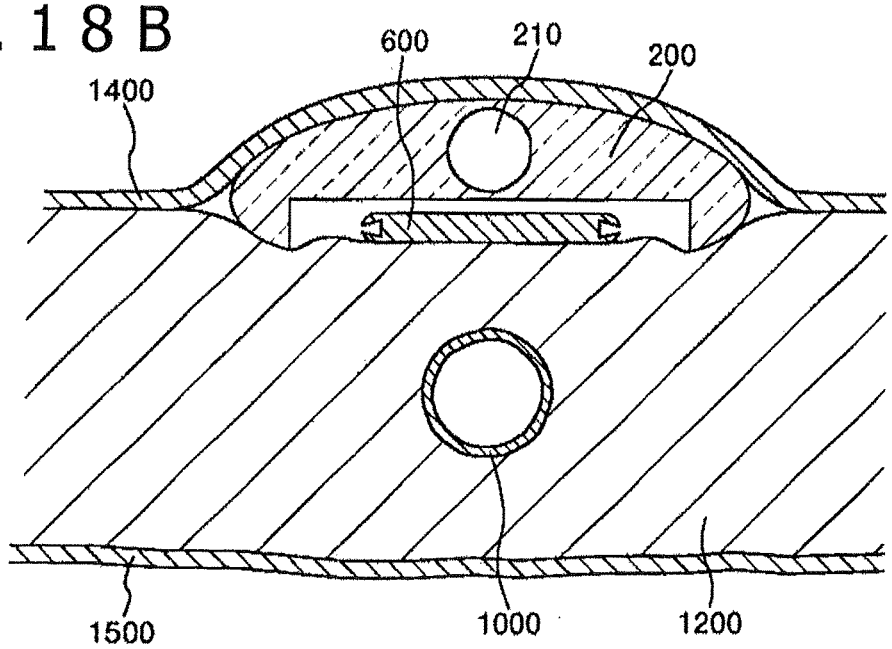

FIGS. 18A and 18B are cross-sectional views showing a blood vessel dissecting device according to a twelfth embodiment of the present disclosure.

Referring to these figures, the twelfth embodiment will be described below. The following detailed description will focus primarily on differences between this twelfth embodiment and the embodiments described above.

This embodiment is the same as the eleventh embodiment described above, except mainly for differences in the configuration of the dissecting device.

As shown in FIG. 18A, a dissecting device 200 in this embodiment is provided with an insertion hole (insertion groove or insertion recess) 280 in which a guide device 600 can be inserted. The insertion hole 280 opens to a surface on one side of the dissecting device 200 (a surface oriented to the side of a great saphenous vein 1000 when the dissecting device 200 is inserted in a living body). In using the blood vessel dissecting device 100 configured in this way, first, the dissecting device 200 is inserted into the living body along the great saphenous vein 1000, as shown in FIG. 18A. Next, as shown in FIG. 18B, the guide device 600 is inserted into the insertion hole 280. By this, the guide device 600 can be rather smoothly disposed in conformity to the tortuous state of the great saphenous vein 1000. Subsequently, the cutting device 300 is inserted into the living body along the guide device 600. This procedure helps ensure that at the time of inserting the cutting device 300, contact between the cutting device 300 and the great saphenous vein 1000 can be prevented from occurring, so that damage to the great saphenous vein 1000 can be avoided or prevented. In addition, the great saphenous vein 1000 can be dissected in a state of being entirely covered substantially evenly with fat 1200. Cutting-away of the fat 1200 in a surplus amount can also be restrained.

By the twelfth embodiment described above, also, the same or equivalent effects to those of the first embodiment described above can be produced.

While the blood vessel dissecting device and the blood vessel dissecting method according to the described aspects of the present disclosure have been described above on the basis of the embodiments illustrated in the drawings, the disclosure is not limited to the embodiments. The configuration of each component can be replaced by any configuration that has a function similar or substantially equivalent to the original. And other structure may be added to the configuration according to the present disclosure. In addition, the embodiments and application examples may be combined in a desired manner.

Figure 19:
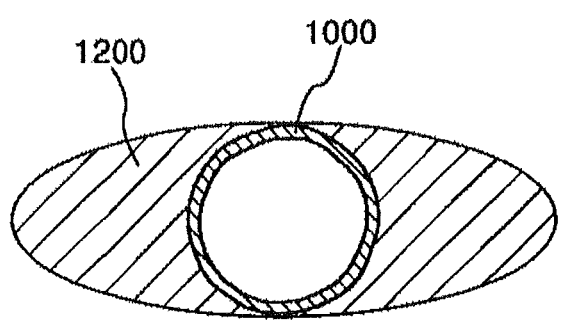
FIG. 19 is a cross-sectional view showing a dissected blood vessel.

While the great saphenous vein is dissected in the state of being covered with fat over the entire perimeter of the vein in the aforementioned embodiments, the great saphenous vein may not necessarily be covered with fat over its entire perimeter. Thus, the great saphenous vein may be dissected in a state where the periphery of the vein is partly covered with fat, or in a state of being not covered with fat. For instance, the great saphenous vein 1000 may be dissected in a state of being covered with flat-shaped fat 1200, as shown in FIG. 19, wherein the fat 1200 present on the upper and lower sides is relatively thin (or the fat 1200 is absent on the upper and lower sides) and wherein the fat 1200 present on the left and right sides is relatively thick. In such a state, the conditions (for example, the presence or absence of damages, shape, twisting, etc.) of the great saphenous vein 1000 can be easily checked and confirmed from above and from below. Consequently, it is possible to use the great saphenous vein 1000 as a bypass vessel or the like after grasping the conditions of the great saphenous vein 1000.

The harvesting of a bypass vessel for use in vascular bypass grafting has been described above in the aforementioned embodiments, but the use of the harvested blood vessel is not limited to the bypass vessel.

The detailed description above describes embodiments of a blood vessel dissecting device and blood vessel dissecting method representing examples of the invention disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A blood vessel dissecting method comprising:
   inserting a dissecting device into a living body along a blood vessel to dissect tissue in a direction along a longitudinal extent of the blood vessel and anchoring the inserted dissecting device to tissue surrounding the blood vessel; and
   after inserting and anchoring the dissecting device, inserting a cutting device into the living body along the blood vessel while using the dissecting device to guide the cutting device to cut the tissue surrounding the blood vessel in the direction of longitudinal extent of the blood vessel such that, after the cutting, an entire perimeter of the blood vessel remains covered with the tissue, wherein the inserting of the dissecting device includes inserting the dissecting device into a boundary of adjacent tissues having different properties, the adjacent tissues having different properties being one of: i) fat and skin; ii) fat and fascia; or iii) fat and bone, wherein the method further comprises dissecting the adjacent tissues having different properties from each other in a thickness direction of the dissecting device.

2. The blood vessel dissecting method according to claim 1, wherein the dissecting device possesses a maximum width that is greater than an outside diameter of the blood vessel.

3. The blood vessel dissecting method according to claim 1, wherein the inserting of the cutting device includes inserting the cutting device on one lateral side of the blood vessel, the method further comprising removing the cutting device from the living body, and thereafter inserting the cutting device into the living body once again on an opposite lateral side of the blood vessel that is opposite the one lateral side.

4. The blood vessel dissecting method according to claim 1, wherein the inserting of the dissecting device includes inserting the dissecting device so that the dissecting device is at a first position between the blood vessel and skin of the living body, the method further comprising removing the dissecting device from the living body while maintaining the cutting device in the living body, and thereafter inserting the dissecting device into the living body once again at a second position opposite the first position, the second position being between the blood vessel and fascia of the living body.

5. The blood vessel dissecting method according to claim 1, further comprising structurally connecting the cutting device to the dissecting device and using the dissecting device to guide movement of the cutting device in the living body.

6. The blood vessel dissecting method according to claim 1, wherein the inserting of the dissecting device into the living body produces a hole in the living body, the method further comprising removing the dissecting device from the living body after inserting the dissecting device into the living body and before inserting the cutting device into the living body, bending the dissecting device in conformity with a shape of the blood vessel to produce a bent dissecting device, and inserting the bent dissecting device into the hole in the living body before inserting the cutting device into the living body.

7. The blood vessel dissecting method according to claim 1, further comprising cutting and stanching branch vessels branching from the blood vessel using the cutting device.

8. The blood vessel dissecting method according to claim 1, wherein the anchoring of the inserted dissecting device to the tissue surrounding the blood vessel comprises moving at least one projection of the dissecting device in an outward direction from a surface of the dissecting device.

9. The blood vessel dissecting method according to claim 8, wherein the surface of the dissecting device faces the blood vessel.

10. The blood vessel dissecting method according to claim 8, wherein the at least one projection comprises a plurality of projections arranged on both sides with respect to a width direction of the dissecting device and in spaced-apart relation along an axial direction of the dissecting device.

11. A blood vessel dissecting method comprising:
inserting a dissecting device into a living body along a blood vessel to dissect tissue in a direction along a longitudinal extent of the blood vessel and anchoring the inserted dissecting device to tissue surrounding the blood vessel; and after inserting and anchoring the dissecting device, inserting a cutting device into the living body along the blood vessel while using the dissecting device to guide the cutting device to cut the tissue surrounding the blood vessel in the direction of longitudinal extent of the blood vessel such that, after the cutting, an entire perimeter of the blood vessel remains covered with the tissue, wherein the inserting of the dissecting device includes inserting the dissecting device into a boundary between fat and skin, wherein the method further comprises dissecting the fat and skin from each other in a thickness direction of the dissecting device.

12. The blood vessel dissecting method according to claim 11, wherein the dissecting device possesses a maximum width that is greater than an outside diameter of the blood vessel.

13. The blood vessel dissecting method according to claim 11, wherein the inserting of the cutting device includes inserting the cutting device on one lateral side of the blood vessel, the method further comprising removing the cutting device from the living body, and thereafter inserting the cutting device into the living body once again on an opposite lateral side of the blood vessel that is opposite the one lateral side.

14. The blood vessel dissecting method according to claim 11, wherein the inserting of the dissecting device includes inserting the dissecting device so that the dissecting device is at a first position between the blood vessel and skin of the living body, the method further comprising removing the dissecting device from the living body while maintaining the cutting device in the living body, and thereafter inserting the dissecting device into the living body once again at a second position opposite the first position, the second position being between the blood vessel and fascia of the living body.

15. The blood vessel dissecting method according to claim 11, further comprising structurally connecting the cutting device to the dissecting device and using the dissecting device to guide movement of the cutting device in the living body.

16. The blood vessel dissecting method according to claim 11, wherein the inserting of the dissecting device into the living body produces a hole in the living body, the method further comprising removing the dissecting device from the living body after inserting the dissecting device into the living body and before inserting the cutting device into the living body, bending the dissecting device in conformity with a shape of the blood vessel to produce a bent dissecting device, and inserting the bent dissecting device into the hole in the living body before inserting the cutting device into the living body.

17. The blood vessel dissecting method according to claim 11, further comprising cutting and stanching branch vessels branching from the blood vessel using the cutting device.

18. The blood vessel dissecting method according to claim 11, wherein the anchoring of the inserted dissecting device to the tissue surrounding the blood vessel comprises moving at least one projection of the dissecting device in an outward direction from a surface of the dissecting device.

19. The blood vessel dissecting method according to claim 18, wherein the surface of the dissecting device faces the blood vessel.

20. The blood vessel dissecting method according to claim 18, wherein the at least one projection comprises a plurality of projections arranged on both sides with respect to a width direction of the dissecting device and in spaced-apart relation along an axial direction of the dissecting device.

* * * * *